US009125868B2

(12) United States Patent
McKinney et al.

(10) Patent No.: US 9,125,868 B2
(45) Date of Patent: *Sep. 8, 2015

(54) METHODS FOR ADMINISTERING WEIGHT LOSS MEDICATIONS

(71) Applicant: OREXIGEN THERAPEUTICS, INC., La Jolla, CA (US)

(72) Inventors: Anthony A. McKinney, San Diego, CA (US); Gary Tollefson, Indianapolis, IN (US); Eckard Weber, San Diego, CA (US); Rick Soltero, Holly Springs, NC (US)

(73) Assignee: OREXIGEN THERAPEUTICS, INC., La Jolla, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/220,349

(22) Filed: Mar. 20, 2014

(65) Prior Publication Data

US 2014/0322318 A1    Oct. 30, 2014

Related U.S. Application Data

(63) Continuation of application No. 12/838,364, filed on Jul. 16, 2010, now Pat. No. 8,722,085, which is a continuation of application No. 11/937,367, filed on Nov. 8, 2007, now abandoned.

(60) Provisional application No. 60/865,159, filed on Nov. 9, 2006.

(51) Int. Cl.
| | |
|---|---|
| *A61K 9/20* | (2006.01) |
| *A61K 31/415* | (2006.01) |
| *A61K 31/137* | (2006.01) |
| *A61K 31/439* | (2006.01) |
| *A61K 31/35* | (2006.01) |
| *A61K 31/551* | (2006.01) |
| *A61P 3/04* | (2006.01) |
| *A61K 31/138* | (2006.01) |
| *A61J 1/03* | (2006.01) |
| *A61J 7/04* | (2006.01) |
| *A61K 31/135* | (2006.01) |
| *A61K 31/42* | (2006.01) |
| *A61K 31/485* | (2006.01) |
| *A61K 45/06* | (2006.01) |
| *A61K 31/423* | (2006.01) |
| *A61K 9/24* | (2006.01) |

(52) U.S. Cl.
CPC ............... *A61K 31/138* (2013.01); *A61J 1/035* (2013.01); *A61J 7/04* (2013.01); *A61K 31/135* (2013.01); *A61K 31/137* (2013.01); *A61K 31/35* (2013.01); *A61K 31/42* (2013.01); *A61K 31/423* (2013.01); *A61K 31/485* (2013.01); *A61K 31/551* (2013.01); *A61K 45/06* (2013.01); *A61J 1/1418* (2015.05); *A61J 7/0454* (2015.05); *A61K 9/209* (2013.01)

(58) Field of Classification Search
USPC .......... 424/464; 514/406, 649, 282, 654, 455, 514/220, 651
See application file for complete search history.

(56) References Cited

U.S. PATENT DOCUMENTS

| | | | |
|---|---|---|---|
| 3,819,706 | A | 6/1974 | Mehta |
| 3,885,046 | A | 5/1975 | Mehta |
| 3,942,641 | A | 3/1976 | Segre |
| 4,089,855 | A | 5/1978 | Chatterjie et al. |
| 4,172,896 | A | 10/1979 | Uno et al. |
| 4,218,433 | A | 8/1980 | Kooichi et al. |
| 4,295,567 | A | 10/1981 | Knudsen |
| 4,483,846 | A | 11/1984 | Koide et al. |
| 4,513,006 | A | 4/1985 | Maryanoff et al. |
| 4,673,679 | A | 6/1987 | Aungst et al. |
| 4,689,332 | A | 8/1987 | McLaughlin et al. |
| 4,828,836 | A | 5/1989 | Elger et al. |
| 4,831,031 | A | 5/1989 | Lowe et al. |
| 4,855,306 | A | 8/1989 | Markstein et al. |
| 4,895,845 | A | 1/1990 | Seed |
| 5,000,886 | A | 3/1991 | Lawter et al. |
| 5,028,612 | A | 7/1991 | Glover |
| 5,082,864 | A | 1/1992 | Van den Oetelaar et al. |
| 5,202,128 | A | 4/1993 | Morella et al. |
| 5,213,807 | A | 5/1993 | Chemburkar et al. |

(Continued)

FOREIGN PATENT DOCUMENTS

| | | |
|---|---|---|
| CA | 2317044 | 7/1999 |
| CL | 200003165 | 11/2000 |

(Continued)

OTHER PUBLICATIONS

Ackerman et al., 1998, Clinical characteristics of response to fluoxetine treatment of obsessive-compulsive disorder. Journal of Clinical Psychopharmacology, 18(3):185-192.

(Continued)

*Primary Examiner* — Kathrien Cruz
(74) *Attorney, Agent, or Firm* — Knobbe, Martens, Olson & Bear LLP

(57) ABSTRACT

Methods and systems for administration of pharmaceuticals using a unit dosage package that includes a first unit dosage that has a first drug and a second drug, a second unit dosage that has the first drug and the second drug, where the second unit dosage includes a different amount of the second drug than the first unit dosage and a unit dosage package is configured to hold the first unit dosage and the second unit dosage. In preferred embodiments the methods and systems are used for administration of weight loss medications.

17 Claims, 10 Drawing Sheets

(56) References Cited

U.S. PATENT DOCUMENTS

| | | |
|---|---|---|
| 5,213,808 A | 5/1993 | Bar-Shalom et al. |
| 5,283,263 A | 2/1994 | Norden |
| 5,312,925 A | 5/1994 | Allen et al. |
| 5,358,970 A | 10/1994 | Ruff et al. |
| 5,364,841 A | 11/1994 | Cooper et al. |
| 5,403,595 A | 4/1995 | Kitchell et al. |
| 5,426,112 A | 6/1995 | Zagon et al. |
| 5,427,798 A | 6/1995 | Ludwig et al. |
| 5,486,362 A | 1/1996 | Kitchell et al. |
| 5,512,593 A | 4/1996 | Dante |
| 5,541,231 A | 7/1996 | Ruff et al. |
| 5,626,874 A | 5/1997 | Conte et al. |
| 5,714,519 A | 2/1998 | Cincotta et al. |
| 5,716,976 A | 2/1998 | Bernstein |
| 5,719,197 A | 2/1998 | Kanios et al. |
| 5,731,000 A | 3/1998 | Ruff et al. |
| 5,738,874 A | 4/1998 | Conte et al. |
| 5,763,493 A | 6/1998 | Ruff et al. |
| 5,817,665 A | 10/1998 | Dante |
| 5,817,666 A | 10/1998 | Katz |
| 5,856,332 A | 1/1999 | Dante |
| 5,866,164 A | 2/1999 | Kuczynski et al. |
| 5,948,799 A | 9/1999 | Cropp |
| 5,958,962 A | 9/1999 | Cook |
| 5,977,099 A | 11/1999 | Nickolson |
| 6,004,970 A | 12/1999 | O'Malley et al. |
| 6,033,686 A | 3/2000 | Seth |
| 6,034,091 A | 3/2000 | Dante |
| 6,048,322 A | 4/2000 | Kushida |
| 6,071,537 A | 6/2000 | Shank |
| 6,071,918 A | 6/2000 | Cook |
| 6,087,386 A | 7/2000 | Chen et al. |
| 6,096,341 A | 8/2000 | Seth |
| 6,110,973 A | 8/2000 | Young |
| 6,120,803 A | 9/2000 | Wong et al. |
| 6,143,327 A | 11/2000 | Seth |
| 6,150,366 A | 11/2000 | Arenson et al. |
| 6,153,223 A | 11/2000 | Apelian et al. |
| 6,183,778 B1 | 2/2001 | Conte et al. |
| 6,191,117 B1 | 2/2001 | Kozachuk |
| 6,197,827 B1 | 3/2001 | Cary |
| 6,210,716 B1 | 4/2001 | Chen et al. |
| 6,238,697 B1 | 5/2001 | Kumar et al. |
| 6,245,766 B1 | 6/2001 | Watsky |
| 6,248,363 B1 | 6/2001 | Patel et al. |
| 6,262,049 B1 | 7/2001 | Coffin et al. |
| 6,274,579 B1 | 8/2001 | Morgan et al. |
| 6,294,192 B1 | 9/2001 | Patel et al. |
| 6,306,436 B1 | 10/2001 | Chungi et al. |
| 6,323,236 B2 | 11/2001 | McElroy |
| 6,342,496 B1 | 1/2002 | Jerussi et al. |
| 6,342,515 B1 | 1/2002 | Masuda et al. |
| 6,344,474 B1 | 2/2002 | Maruani et al. |
| 6,369,113 B2 | 4/2002 | Young |
| 6,383,471 B1 | 5/2002 | Chen et al. |
| 6,387,956 B1 | 5/2002 | Shapira et al. |
| 6,420,369 B1 | 7/2002 | Marcotte |
| 6,437,147 B1 | 8/2002 | Andersen et al. |
| 6,441,038 B1 | 8/2002 | Loder et al. |
| 6,451,860 B1 | 9/2002 | Young |
| 6,462,237 B1 | 10/2002 | Gidwani et al. |
| 6,500,459 B1 | 12/2002 | Chhabra et al. |
| 6,506,799 B1 | 1/2003 | Dasseux |
| 6,514,531 B1 | 2/2003 | Alaux et al. |
| 6,528,520 B2 | 3/2003 | Clemens |
| 6,541,478 B1 | 4/2003 | O'Malley et al. |
| 6,548,551 B2 | 4/2003 | Hinz |
| 6,569,449 B1 | 5/2003 | Stinchcomb et al. |
| 6,576,256 B2 | 6/2003 | Liang et al. |
| 6,589,553 B2 | 7/2003 | Li et al. |
| 6,622,036 B1 | 9/2003 | Suffin |
| 6,627,223 B2 | 9/2003 | Percel et al. |
| 6,630,165 B2 | 10/2003 | Seroff et al. |
| 6,638,535 B2 | 10/2003 | Lemmens et al. |
| 6,652,882 B1 | 11/2003 | Odidi et al. |
| 6,682,759 B2 | 1/2004 | Lim et al. |
| 6,686,337 B2 | 2/2004 | Connor |
| 6,706,283 B1 | 3/2004 | Appel et al. |
| 6,713,488 B2 | 3/2004 | Sadee et al. |
| 6,797,283 B1 | 9/2004 | Edgren et al. |
| 6,893,660 B2 | 5/2005 | Li et al. |
| 6,893,661 B2 | 5/2005 | Odidi et al. |
| 6,905,708 B2 | 6/2005 | Li et al. |
| 6,923,988 B2 | 8/2005 | Patel et al. |
| 6,926,907 B2 | 8/2005 | Plachetka |
| 6,995,169 B2 | 2/2006 | Chapleo et al. |
| 7,109,198 B2 | 9/2006 | Gadde et al. |
| 7,375,111 B2 | 5/2008 | Weber et al. |
| 7,422,110 B2 | 9/2008 | Zanden et al. |
| 7,425,571 B2 | 9/2008 | Gadde et al. |
| 7,429,580 B2 | 9/2008 | Gadde et al. |
| 7,462,626 B2 | 12/2008 | Weber et al. |
| 7,682,633 B2 | 3/2010 | Matthews et al. |
| 7,754,748 B2 | 7/2010 | Gadde et al. |
| 8,088,786 B2 | 1/2012 | McKinney et al. |
| 8,318,788 B2 | 11/2012 | McKinney et al. |
| 8,722,085 B2 | 5/2014 | McKinney et al. |
| 8,969,371 B1 | 3/2015 | Klassen et al. |
| 2001/0025038 A1 | 9/2001 | Coffin et al. |
| 2001/0046964 A1 | 11/2001 | Percel et al. |
| 2002/0012680 A1 | 1/2002 | Patel et al. |
| 2002/0019364 A1 | 2/2002 | Renshaw |
| 2002/0022054 A1 | 2/2002 | Sawada et al. |
| 2002/0025972 A1 | 2/2002 | Hinz |
| 2002/0037836 A1 | 3/2002 | Henriksen |
| 2002/0044962 A1 | 4/2002 | Cherukuri et al. |
| 2002/0055512 A1 | 5/2002 | Marin et al. |
| 2002/0090615 A1 | 7/2002 | Rosen et al. |
| 2002/0198227 A1 | 12/2002 | Bernstein |
| 2003/0003151 A1 | 1/2003 | Chopra |
| 2003/0017189 A1 | 1/2003 | Wong et al. |
| 2003/0035840 A1 | 2/2003 | Li et al. |
| 2003/0044462 A1 | 3/2003 | Subramanian et al. |
| 2003/0054031 A1 | 3/2003 | Li et al. |
| 2003/0054041 A1 | 3/2003 | Lemmens et al. |
| 2003/0055008 A1 | 3/2003 | Marcotte |
| 2003/0055038 A1 | 3/2003 | Howard et al. |
| 2003/0068371 A1 | 4/2003 | Oshlack et al. |
| 2003/0087896 A1 | 5/2003 | Glover |
| 2003/0091630 A1 | 5/2003 | Louie-Helm et al. |
| 2003/0109546 A1 | 6/2003 | Fenton |
| 2003/0130322 A1 | 7/2003 | Howard |
| 2003/0133982 A1 | 7/2003 | Heimlich et al. |
| 2003/0133985 A1 | 7/2003 | Louie-Helm et al. |
| 2003/0135056 A1 | 7/2003 | Anderson et al. |
| 2003/0144174 A1 | 7/2003 | Brenna et al. |
| 2003/0144271 A1 | 7/2003 | Shulman |
| 2003/0147952 A1 | 8/2003 | Lim et al. |
| 2003/0161874 A1 | 8/2003 | Li et al. |
| 2003/0198683 A1 | 10/2003 | Li et al. |
| 2003/0215496 A1 | 11/2003 | Patel et al. |
| 2004/0002462 A1 | 1/2004 | Najarian |
| 2004/0005368 A1 | 1/2004 | Mann et al. |
| 2004/0022852 A1 | 2/2004 | Chopra |
| 2004/0029941 A1 | 2/2004 | Jennings |
| 2004/0047908 A1 | 3/2004 | Lemmens et al. |
| 2004/0059241 A1 | 3/2004 | Suffin |
| 2004/0092504 A1 | 5/2004 | Benja-Athon |
| 2004/0096499 A1 | 5/2004 | Vaya et al. |
| 2004/0101556 A1 | 5/2004 | Li et al. |
| 2004/0105778 A1 | 6/2004 | Lee et al. |
| 2004/0106576 A1 | 6/2004 | Jerussi et al. |
| 2004/0115134 A1 | 6/2004 | Merisko-Liversidge |
| 2004/0122033 A1 | 6/2004 | Nargund et al. |
| 2004/0158194 A1 | 8/2004 | Wolff et al. |
| 2004/0185097 A1 | 9/2004 | Kannan et al. |
| 2004/0204472 A1 | 10/2004 | Briggs et al. |
| 2004/0228915 A1 | 11/2004 | Noack et al. |
| 2004/0228924 A1 | 11/2004 | Oshlack et al. |
| 2004/0242974 A1 | 12/2004 | Glover |
| 2004/0258757 A1 | 12/2004 | Bosch et al. |
| 2005/0004106 A1 | 1/2005 | Romano |
| 2005/0013863 A1 | 1/2005 | Lim et al. |
| 2005/0019385 A1 | 1/2005 | Houze |

(56) References Cited

U.S. PATENT DOCUMENTS

| | | |
|---|---|---|
| 2005/0019409 A1 | 1/2005 | Edgren et al. |
| 2005/0019412 A1 | 1/2005 | Bosch et al. |
| 2005/0026977 A1 | 2/2005 | Jennings |
| 2005/0026986 A1 | 2/2005 | Maruani et al. |
| 2005/0031691 A1 | 2/2005 | McGurk et al. |
| 2005/0043704 A1 | 2/2005 | Lieberburg |
| 2005/0043705 A1 | 2/2005 | Lieberburg |
| 2005/0043773 A1 | 2/2005 | Lieberburg |
| 2005/0063913 A1 | 3/2005 | Pruitt et al. |
| 2005/0096311 A1 | 5/2005 | Suffin et al. |
| 2005/0112198 A1 | 5/2005 | Challapalli et al. |
| 2005/0112211 A1 | 5/2005 | Gervais et al. |
| 2005/0118268 A1 | 6/2005 | Percel et al. |
| 2005/0137144 A1 | 6/2005 | Gadde et al. |
| 2005/0142195 A1 | 6/2005 | Li et al. |
| 2005/0143322 A1 | 6/2005 | Gadde et al. |
| 2005/0147664 A1 | 7/2005 | Liversidge et al. |
| 2005/0154002 A1 | 7/2005 | Crooks et al. |
| 2005/0163840 A1 | 7/2005 | Sawada et al. |
| 2005/0181049 A1 | 8/2005 | Dong et al. |
| 2005/0214368 A1 | 9/2005 | Kawakami et al. |
| 2005/0214371 A1 | 9/2005 | Di Capua et al. |
| 2005/0214372 A1 | 9/2005 | Di Capua et al. |
| 2005/0215552 A1 | 9/2005 | Gadde et al. |
| 2005/0232990 A1 | 10/2005 | Boehm et al. |
| 2005/0238718 A1 | 10/2005 | Oberegger et al. |
| 2005/0245460 A1 | 11/2005 | Meyerson et al. |
| 2005/0250838 A1 | 11/2005 | Challapalli et al. |
| 2005/0277579 A1 | 12/2005 | Krishnan et al. |
| 2006/0009514 A1 | 1/2006 | Gadde et al. |
| 2006/0018933 A1 | 1/2006 | Vaya et al. |
| 2006/0018934 A1 | 1/2006 | Vaya et al. |
| 2006/0024365 A1 | 2/2006 | Vaya et al. |
| 2006/0051418 A1 | 3/2006 | Cowen et al. |
| 2006/0058293 A1 | 3/2006 | Weber et al. |
| 2006/0069086 A1 | 3/2006 | Michalow |
| 2006/0079501 A1 | 4/2006 | Krishnan et al. |
| 2006/0100205 A1 | 5/2006 | Weber et al. |
| 2006/0122127 A1 | 6/2006 | Rao et al. |
| 2006/0160750 A1 | 7/2006 | Krishnan et al. |
| 2006/0246131 A1 | 11/2006 | Cottinham |
| 2006/0276412 A1 | 12/2006 | Tollefson |
| 2007/0078135 A1 | 4/2007 | Yuan et al. |
| 2007/0099947 A1 | 5/2007 | Dean et al. |
| 2007/0117827 A1 | 5/2007 | Tollefson et al. |
| 2007/0128298 A1 | 6/2007 | Cowley et al. |
| 2007/0129283 A1 | 6/2007 | McKinney et al. |
| 2007/0148237 A1 | 6/2007 | McKinney et al. |
| 2007/0149451 A1 | 6/2007 | Holmes |
| 2007/0179168 A1 | 8/2007 | Cowley et al. |
| 2007/0185084 A1 | 8/2007 | McKinney et al. |
| 2007/0270450 A1 | 11/2007 | Weber et al. |
| 2007/0275970 A1 | 11/2007 | Weber et al. |
| 2007/0281021 A1 | 12/2007 | McKinney et al. |
| 2008/0027487 A1 | 1/2008 | Patel et al. |
| 2008/0058407 A1 | 3/2008 | Baron et al. |
| 2008/0110792 A1 | 5/2008 | McKinney et al. |
| 2008/0214592 A1 | 9/2008 | Cowley et al. |
| 2009/0018115 A1 | 1/2009 | Gadde et al. |
| 2009/0076108 A1 | 3/2009 | Gadde et al. |
| 2010/0166889 A1 | 7/2010 | Sanfilippo |
| 2010/0190793 A1 | 7/2010 | Weber et al. |
| 2011/0028505 A1 | 2/2011 | McKinney et al. |
| 2011/0098289 A1 | 4/2011 | Gadde et al. |
| 2011/0144145 A1 | 6/2011 | Tollefson |
| 2011/0172260 A1 | 7/2011 | Dunayevich et al. |
| 2012/0010232 A1 | 1/2012 | Weber et al. |
| 2013/0177602 A1 | 7/2013 | McKinney et al. |
| 2013/0245055 A1 | 9/2013 | Wright |
| 2013/0252995 A1 | 9/2013 | Dunayevich et al. |
| 2014/0080857 A1 | 3/2014 | McKinney et al. |
| 2014/0364468 A1 | 12/2014 | Gadde et al. |
| 2015/0080424 A1 | 3/2015 | McKinney et al. |
| 2015/0119417 A1 | 4/2015 | Tollefson |

FOREIGN PATENT DOCUMENTS

| | | |
|---|---|---|
| CL | 200500308 | 2/2001 |
| CL | 2004-00851 | 4/2004 |
| CL | 200700113 | 1/2007 |
| EP | 0 005 636 | 11/1979 |
| EP | 0 294 028 | 12/1988 |
| EP | 0 442 769 | 8/1991 |
| EP | 0 541 192 | 5/1993 |
| EP | 0 598 309 | 5/1994 |
| EP | 1 275 373 | 1/2003 |
| EP | 1 759 701 | 7/2007 |
| EP | 1 813 276 | 8/2007 |
| JP | 2003-509349 | 3/2003 |
| RU | 2214241 | 10/2003 |
| WO | WO 83/03197 | 9/1983 |
| WO | WO 90/13294 | 11/1990 |
| WO | WO 94/20100 | 9/1994 |
| WO | WO 96/09047 | 3/1996 |
| WO | WO 97/06786 | 2/1997 |
| WO | WO 97/06787 | 2/1997 |
| WO | WO 97/41873 | 11/1997 |
| WO | WO 98/00130 | 1/1998 |
| WO | WO 99/16375 | 4/1999 |
| WO | WO 99/37305 | 7/1999 |
| WO | WO 99/38504 | 8/1999 |
| WO | WO 00/50020 | 8/2000 |
| WO | WO 00/51546 | 9/2000 |
| WO | WO 00/61139 | 10/2000 |
| WO | WO 00/62757 | 10/2000 |
| WO | WO 00/76493 | 12/2000 |
| WO | WO 01/01973 | 1/2001 |
| WO | WO 01/26641 | 4/2001 |
| WO | WO 01/52833 | 7/2001 |
| WO | WO 01/52851 | 7/2001 |
| WO | WO 01/58447 | 8/2001 |
| WO | WO 01/58451 | 8/2001 |
| WO | WO 01/62257 | 8/2001 |
| WO | WO 01/78725 | 10/2001 |
| WO | WO 01/85257 | 11/2001 |
| WO | WO 02/09694 | 2/2002 |
| WO | WO 02/24214 | 3/2002 |
| WO | WO 02/087590 | 11/2002 |
| WO | WO 03/013524 | 2/2003 |
| WO | WO 03/013525 | 2/2003 |
| WO | WO 03/013479 | 3/2003 |
| WO | WO 03/092682 | 11/2003 |
| WO | WO 03/097051 | 11/2003 |
| WO | WO 2004/002463 | 1/2004 |
| WO | WO 2004/009015 | 1/2004 |
| WO | WO 2004/024096 | 3/2004 |
| WO | WO 2004/052289 | 6/2004 |
| WO | WO 2004/054570 | 7/2004 |
| WO | WO 2004/054571 | 7/2004 |
| WO | WO 2004/071423 | 8/2004 |
| WO | WO 2004/091593 | 10/2004 |
| WO | WO 2004/100956 | 11/2004 |
| WO | WO 2004/100992 | 11/2004 |
| WO | WO 2004/110368 | 12/2004 |
| WO | WO 2004/110375 | 12/2004 |
| WO | WO 2005/000217 | 1/2005 |
| WO | WO 2005/077362 | 2/2005 |
| WO | WO 2005/032555 | 4/2005 |
| WO | WO 2005/049043 | 6/2005 |
| WO | WO 2005/079773 | 9/2005 |
| WO | WO 2005/089486 | 9/2005 |
| WO | WO 2006/049941 | 5/2006 |
| WO | WO 2006/052542 | 5/2006 |
| WO | WO 2006/055854 | 5/2006 |
| WO | WO 2006/088748 | 8/2006 |
| WO | WO 2007/012064 | 1/2007 |
| WO | WO 2007/047351 | 4/2007 |

(56) References Cited

FOREIGN PATENT DOCUMENTS

| | | |
|---|---|---|
| WO | WO 2007/085637 | 8/2007 |
| WO | WO 2008/119978 | 10/2008 |
| WO | WO 2013/184837 | 12/2013 |

OTHER PUBLICATIONS

Albaugh et al., 2005, Topiramate prevents the rapid weight gain and adiposity in a model of atypical antipsychotic drug-induced obesity, Fed. of American Soc. for Experimental Biology, 19(5, Suppl. S, Part 2):A1130.
Altman et al., 2005, Standard Deviations and Standard Errors, BMJ, 331:903.
Anderson et al., 2002, Bupropion SR enhances weight loss: a 48-week double-blind, placebo-controlled trial, Obesity R., 10(7):633-641.
Appolinario et al., 2004, Pharmacological Approaches in the Treatment of Binge Eating Disorder, Current Drug Targets, 5:301-307.
Aronne et al., 2003, Weight gain in the treatment of mood disorders, J. Clin Psychiatry, 64(suppl 8).
Asconape, 2002, Some Common Issues in the Use of Antiepileptic Drugs, Seminars in Neurology; 22(1):27-39.
Astrup et al., Mar. 1991, Thermogenic Synergism Between Ephedrine and Caffeine in Healthy Volunteers: A Double-Blind, Placebo-Controlled Study, Metabolism, 40(3):323-329.
Atkinson et al. (Oct. 1985) Effects of long-term therapy with naltrexone on body weight in obesity, Clinical Pharmacology & Therapeutics, 38:419-422.
Atkinson, 2003, Clinical Guidelines on the identification, Evaluation, and pharmacologic treatment of obesity in Adults, Online, 07-25, URL:http://www.endotext.org.obesity/obesity15b/obesity15b.htm.
Ayala (2000) Weight Loss Associated With the Administration of Zonisamide, AES Proceedings, Epilepsia 41(Suppl. 7) :99—No. 2.041.
Ayala et al., Dec. 1-6, 2000, Weight loss associated with the administration of zonisamide, a compendium of posters and platform session for ZonegranTM and Diastat®, Annual Meeting 2000 of the American Epilepsy Society, Los Angeles, CA.
Baldassano et al. (2006) Acute treatment of bipolar depression with adjunctive zonisamide: a retrospective chart review, Disorders 6:432-434.
Barr et al. 1993. The serotonin hypothesis of obsessive compulsive disorder. International Clinical Psychopharmacology, 8(2):79-82.
Bastani et al. 1991. Serotonin uptake and imipramine binding in the blood platelets of obsessive-compulsive disorder patients. Biol. Psychiatry, 30:131-139.
Bays et al., Aug. 1, 2007, Adiposopathy: treating pathogenic adipose tissue to reduce cardiovascular disease risk, Current Treatment Options in Cardiovascular Medicine, 9(4):259-271.
Beelen et al. (2001) Asymptomatic QTC prolongation associated with queitiapine fumarate overdose in a patient being treated with risperidone, Human & Experimental Toxicology 20:215-219.
Benjamin et al. 1993. Naltrexone and fluoxetine in Prader-Willi syndrome. J. Am. Acad. Child Adolesc. Psychiatry, 32(4):870-873.
Bergeron et al. 2002. Sertraline and fluoxetine treatment of obsessive-compulsive disorder: Results of a double-blind, 6-month treatment study. Journal of Clinical Psychopharmacology, 22(2):148-154.
Berke et al. (Jul. 15, 2000) Medical Management of Obesity, American Academy of Family Physicians, 62(2):419-26 Abstract.
Billett et al. 1997. Obsessive compulsive disorder, response to serotonin reuptake inhibitors and the serotonin transporter gene. Molecular Psychiatry, 2:403-406.
Blanchard et al. (2003) Pancreatitis Treated with Didanosine and Tenofabir Disoproxil Fumarate Clinical Infectious Diseases, 37:57-62.
Broocks et al. 1998. Higher prevalence of obsessive-compulsive symptoms in patients with blepharospasm than in patients with hemifacial spasm. Am. J. Psychiatry, 155:555-557.
Bupropion (Oral Route), MayoClinic.com, 19 pp., 2009.
Calabrese et al. (Sep. 2000) Letters to the Editors, Lamotrigine and Clozapine for Bipolar Disorder, American J. of Psychiatry, 157:1523.
Carlsen et al. (Jan 1998) Evidence for dissociation of insulin-and weight-reducing effects of metformin in non-diabetic male patients with coronary heart disease, Diabetes Research and Clinical Practice Amersterdam, 39(1):47-54.
Carpenter et al. (Jan. 1, 1999) Mirtazapine Augmentation in the Treatment of Refractory Depression, J Clin Psychiatry, 60:1.
Carrion, 1995. Naltrexone for the treatment of trichotillomania: A case report. J. Clin. Psychopharmacol., 15(6):444-445.
Carroll (2003) Medicinal Chemistry Division Award Address: Monoamine Transporters and Opioid Receptors. Targets for Addiction Therapy, J. Med. Chem; 46(10):1775-1794.
Carter et al. 2003. Pharmacologic treatment of binge-eating disorder. Primary Psychiatry, 10(10)31-36.
Cash et al. (2000) Attitudes about antidepressants: Influence of information about weight-related side effects, Perceptual and Motor Skills, 90:453-456.
Casner et al. 1996. Naltrexone and self-injurious behavior: A retrospective population study. Journal of Clinical Psychopharmacology, 16(5):389-394.
Chen et al. (Jan. 2004) Synergistic Effects of Cannabinoid inverse agonist AM251 and opioid antagonist nalmefene on food intake, Brain Res, 999:22-230.
Chen et al., 2005, Combination treatment of clozapine and topiramate in resistant rapid-cycling bipolar disorder, Clin. Neuropharmacol. 28(3):136-138.
Chen et al., Jun. 2003, Nonketotic hyperosmolar syndrome from olanzapine, lithium, and valproic acid cotreatment, Annals of Pharmacotherapy, 37(6):919-920.
Chengappa et al. (2002) Changes in body Weight and Body mass index among psychiatric patients receiving lithium, valproate, or topiramate: an open-label, nonrandomized chart review, Clinical Therapeutics, 24(10):1576-1584.
Ching, Mar. 1980, Influence of diphenylhydantoin upon oral glucose tolerance test in obesity, Chinese Medical Journal, 27(1):432-439.
Chouinard et al. 1996. Potentiation of fluoxetine by aminoglutethimide, an adrenal steroid suppressant, in obsessive-compulsive disorder resistant to SSRIs: A case report. Prog. Neuro-Psychopharmacol. & Biol. Psychiat., 20:1067-1079.
Clapham et al. (2001) Anti-obesity drugs: a critical review of current therapies and future opportunities. Pharmacology & Therapeutics. 89:81-121.
Clark et al., 2003, Diabetes mellitus associated with atypical antipsychotic medications, Diabetes Technology & Therapeutics, 5(4):669-683.
Clinical Trial: Drug Treatment for Depressed Alcoholics (Naltrexone/Fluoxetine). (n.d.) Retrieved Jun. 28, 2007, from http://www.clinicaltrials.gov/ct/show/NCT00006204;jsessionid+FED6D0856E098BC0B1940E464179B71B?order=28.
Colosimo, et al. 1999. Motor fluctuations in Parkinson's disease: Pathophysiology and treatment. European Journal of Neurology, 6:1-21.
Cone et al. (2001) The arcuate nucleus as a conduit for diverse signals relevant to energy homeostasis, Int'l Journal of Obesity, 25(5):S63-S67.
Croft et al. (Apr. 2002) Effect on body weight of bupropion sustained-release in patients with major depression treated for 52 weeks, Clinical Therapeutics 24(4):662-672.
Cuparencu et al., 1993, Effects of some benzodiazepines on glycemia in albino rats, Romanian Journal of Physiology, 30(1-2):7-15 (abstract).
Dechant et al. (1991) Drugs, 41:225-253.
Dembowski et al. (2003) Successful Antimanic Treatment and Mood Stabilization with Lamotrigine, Clozapine, and Valproate in a Bipolar Patient after Lithium-induced Cerebellar Deterioration, Letter Pharmacopsychiatry, 36:83-86.
Deshmukh et al. (Jul. 2003) Managing weight gain as a side effect of antidepressant therapy, Cleveland Clinic Journal of Medicine, vol. 70.
DeSimone et al. (2005) Carbonic anhydrase inhibitors. Zonisamide is an effective inhibitor of the cytosolic isozyme II and mitochondrial

(56) References Cited

OTHER PUBLICATIONS isozyme V: Solution and x-ray crystallographic studies, Bioorganic & Medicinal Chemistry Letters, 15:2315-2320.
Devlin et al. (2000) Open treatment of overweight binge eaters with phentermine and fluoxetine as an adjunct to cognitive-behavioral therapy. Int. J. Eating Disord; 28:325-332.
Durgin et al., 2005, Pharmaceutical Practice for Technicians, 3rd Edition, Thomson Delmar Learning, p. 174.
Dursun et al. (2001) Accelerated Weight Loss After Treating Refractory Depression with Fluoxetine Plus Topiramate: Possible Mechanism of Action, Canadian Journal of Psychiatry, 46(3):287-288.
Dursun et al. (2001) Augmenting Antipsychotic treatment with Lamotrigine or topiramate in patients with treatment-resistant Schizophrenia: a naturalistic case-series outcome study Journal of Psychopharmacology 15(4):297-301.
Dursun et al. (2001) Psychopharmacology for the Clinician Psychopharmacologie Pratiqu, Journal of Psychiatry Neuroscience, 26(2):168.
Dursun et al. (Oct. 1999) Clozapine Plus Lamotrigine in Treatment-Resistant Schizophrenia, Arch Gen Psychiatry, 56:950-951.
Dwyer et al., 2002, Psychoactive drugs affect glucose transport and the regulation of glucose metabolism, International Review of Neurobiology, 51:503-530.
El-Haschimi et al. 2000. Two defects contribute to hypothalamic leptin resistance in mice with diet-induced obesity. The Journal of Clinical Investigation, 105(12):1827-1832.
Erez et al., 1982, Narcotic antagonistic potency of bivalent ligands which contain β-naltrexamine. Evidence for bridging between proximal recognition sites, J. Med. Chem., 25:847-849.
Erfurth et al., Mar. 2002, Bupropion as add-on strategy in difficult-to-treat bipolar depressive patients, Neurophsychobiology, 45(Supplement 1):33-36.
Erzegovesi et al. 2001. Clinical predictors of drug response in obsessive-compulsive disorder. Journal of Clinical Psychopharmacology, 21(5):488-492.
Esposito-Avella et al. (Jan. 1973) Studies on the protective effect of diphenylhyndantoin against alioxan diabetes in mice, Proceedings of the Society for Experimental Biology & Medicine, 142(1):82-85.
Ettmayer et al, May 6, 2004, Lessons learned from marketed and investigational prodrugs, J. Med. Chem, 47(10):2393-2404.
Faught et al. (2001) Randomized Controlled Trial of Zonisamide for the Treatment of Refractory Partial-Onset Seizures., Neurology; 57(10):1774-1779.
Fava, 2000, Weight Gain and Antidepressants. J Clin Psychiatry; 61(suppl 11):37-41.
Ferre et al. (1996) Correction of diabetic alterations by glucokinase. Proc. Natl. Acad. Sci. USA, 93:7225-7230.
Ferre et al. (1996) Evidence from transgenic mice that glucokinase is rate limiting for glucose utilization in the liver, The FASEB Journal, 10:1213-1218.
Fingl et al., The Pharmacological Basis of Therapeutics. Chapter 1: General Principles, pp. 1-46 (1975).
Fontela et al., Mar. 1986, Blocking effect of naloxone, dihydroergotamine and adrenalectomy in lithium-induced hyperglycaemia and glucose intolerance in the rate, Acta Endocrinologica, 111(3):342-348 (abstract).
Fukagawa et al. (Nov. 2001) Monoaminergic anorectic agents, Nippon Yikurigaku Zasshi, 118(5):303-8, 2001 Abstract.
Fulghesu et al. (Aug. 1993) Long-term naltrexone treatment reduces the exaggerated insulin secretion in patients with polycystic ovary disease, Obstetrics & Gynecology, 82(2):191-197.
Fuller et al. (1989) Fluoxetine: A Serotonergic Appetite Suppressant Drug, Drug Development Research, 17(1):1-15.
Gadde et al, "Zonisamide in Obesity: A 16-Week Randomized Trial", No. NR473, New Research, American Psychiatric Association 2002 Annual Meeting, May 18-23, 2002, Philadelphia, Pennsylvania (abstract).
Gadde et al, Randomized Trial of Weight Loss Efficacy of Zonisamide, No. 304, 26(Suppl. 1), Journal of the International Association for the Study of Obesity, Ninth International Congress on Obesity, Sao Paolo, Brazil, Aug. 24-29, 2002.
Gadde et al. "Bupropion for Weight Loss: An Investigation of Efficacy and Tolerability in Overweight and Obese Women" Obesity Research 9 (9): 544-551 (2001).
Gadde et al. , "Zonisamide for Weight Loss in Obese Adults—A Randomized Controlled Trial" JAMA 289 (14): 1820-1825 (2003).
Gadde et al., 2002, Randomized controlled trial of zonisamide for treating obesity, Epilepsia 43 Suppl. 7:218 (abstract).
Gadde et al., 2003, Zonisamide enhances weight loss in patients with obesity. Inpharma, 1383(84):9.
Gadde et al., May 1999, Bupropion Sustained Release in Obesity: A Randomized Double-Blind, Placebo-Controlled Study, No. NR634, New Research Program & Abstracts, American Psychiatric Association, 1999 Annual Meeting, The Clinician, Washington, D.C.
Gadde et al., Sep. 1999, A randomized double-blind placebo-controlled study of bupropion sustained release in obesity, European Neuropsychopharmacology, 9(5):366.
Gatley et al.,1996, $^{123}$I-labeled AM251: a radioiodinated ligand which binds in vivo to mouse brain cannabinoid $CB_1$ receptors. European Journal of Pharmacology; 307:331-338.
Gehlert et al. (Oct. 1998) The Selective Norepinephrine Reuptake Inhibitor, LY368975, Reduces Food Consumption in Animal Models of Feeding, J. Pharmacology and Experimental Therapeutics, 87(1):122-7 Abstract.
Gerich et al. (1972) In vitro inhibition of pancreative glucagon secretion by diphenylhydantoin, Journal of Clinical Endocrinology and Metabolism 35(6):823-823.
Gerra et al. 1995. Hostility in heroin abusers subtypes: Fluoxetine and naltrexone treatment. Prog. Neuro-Psychopharmacol. & Biol. Psychiat., 19:1225-1237.
Gerra et al., Sep. 30, 2006, Effects of olanzapine on aggressiveness in heroin dependent patients, Progress in Neuro-Psychopharmacology & Biological Psychiatry, 30(7):1291-1298.
Ginsberg et al. (2000) Effects of Mood Stabilizers on Weight, Primary Psychiatry 7(5):49-58.
Givens et al. (1987) Reduction of hyperinsulinemia and insulin resistance by opiate receptor blockade in the polycystic ovary syndrome with acanthosis nigricans, Journal of Clinical Endocrinology and Metabolism, 64(2):377-382.
Glass et al., 1999, Opioids and food intake: distributed functional neural pathways?, Neuropeptides, 33(5):360-368.
Goldstein et al. (Mar. 1994) Fluoxetine: a randomized clinical trial in the treatment of obesity, International Journal of Obesity and Related Metabolic Disorders, 17(3):129-135, CAS accession #9424430.
Goodman et al. 1989. The Yale-Brown obsessive compulsive scale. Arch. Gen. Psychiatry, 46:1006-1011.
Gordon et al. (Jun. 1999) Mood Stabilization and Weight Loss with Topiramate American Journal of Psychiatry, American Psychiatric Association, Washington D.C., 156(6):968-969.
Grady (Mar. 15, 2003) Quest for Weight-Loss Drug Takes an Unusual Turn, The New York Times—Health, www.nytimes.com, 3 pp.
Grant et al. 2004. Impulse control disorders: Clinical characteristics and pharmacological management. Annals of Clinical Psychiatry, 16:27-34.
Grant et al. 2004. Pharmacotherapy outcome in older pathological gamblers: A preliminary investigation. Journal of Geriatric Psychiatry and Neurology, 17(1):9-12.
Grant et al. 2006. Compulsive aspects of impulse-control disorders. Psychiatr. Clin. North Am., 29(2):539-x.
Greenberg et al. 1998. Delayed obsessive-compulsive disorder symptom exacerbation after a single dose of a serotonin antagonist in fluoxetine-treated but not untreated patients. Psychopharmacology, 140:434-444.
Greenway et al. (2000) A Long-acting Leptin Analog does not Enhance Fat, Visceral Fat, or Weight Loss When Combined with Caffeine Ephedrine in Obese Subjects, International Journal of Obesity, S136.
Greenway et al. (Jul. 1999) Double-Blind, Randomized, Placebo-Controlled Clinical Trials with Nonprescription Medications for the Treatment of Obesity, Obesity Research, 7(4):370-78.

(56) References Cited

OTHER PUBLICATIONS

Greenway et al., Dec. 2009, Comparison of combined bupropion and naltrexone therapy for obesity with monotherapy and placebo, J. Clin Endocrinol Metab, 94(12):4898-4906.

Greenway et al., Jan. 2009, Rational design of a combination medication for the treatment of obesity, Obesity, 17(1):30-39.

Greenway et al., Jun. 2006, Bupropion and naltrexone for the treatment of obesity, Diabetes: Abstract Book: 66th Scientific Sessions, 55(Supplement 1):A394.

Greenway et al., Jun. 2006, Bupropion and naltrexone for the treatment of obesity, poster, 1 pg.

Greist et al. (Apr. 1995) Double-blind Parallel Comparison of Three Dosages of Sertraline and Placebo in Outpatients With Obsessive-compulsive Disorder, Arch Gen Psychiatry, 52:289-295.

Grunenthal, Neo-Eunomin Gebrauschsinformation, Neunomin Prescription Information, Feb. 2004, pp. 1-2.

Hagan et al., Dec. 1997, Combined naloxone and fluoxetine on deprivation-induced binge eating of palatable foods in rats, Pharmacol Biochem Behav, 58(4):1103-1107.

Hahn et al. (1985) Irreversible opiate agonists and antagonists. III. Phenylhydrazone derivatives of naloxone and oxymorphone. J. Pharm. Exper. Therapeutics; 235:846-850.

Halpern et al., Jul. 27, 2010, Combinations of drugs in the treatment of obesity, Pharmaceuticals, 3:2398-2415.

Hamidi et al. 2007. Naltrexone in obsessive-compulsive disorder: An open-label trial. Iranian Journal of Psychiatry and Behavioral Sciences, 1(1):16-21.

Harrison's Principles of Internal Medicine, Braunwald et al., The epilepsies and convulsive disorders, Eleventh Edition, McGraw-Hill Book Company, pp. 1921-1930 (1987).

Hashiguti et al. (1993) Simultaneous determination of in vivo hydroxylation of tyrosine and tryptophan in rat striatum by microdialysis-HPLC: relationship between dopamine and serotonin biosynthesis; Journal of Neural Transmission, 93:213-223.

Hollander et al. 1991. Effects of chronic fluoxetine treatment on behavioral and neuroendocrine responses to meta-chlorophenylpiperazine in obsessive-compulsive disorder. Psychiatry Research, 36:1-17.

Hussey et al., 2002, Synthesis of a β-estradiol-biotin chimera that potently heterodimerizes estrogen receptor and streptavidin proteins in a yeast three-hybrid system, J. Am. Chem. Soc., 125:3692-3693.

Insulin Resistance and Pre-diabetes, http://diabetes.niddk.hih.gov/DM/pubs/insulineresistance/, NIH Publication No. 09/4893, Oct. 2008, 9 pp.

Islam et al., 1994, Naltrexone, Serotonin Receptor Subtype Antagonists, and Carbohydrate Intake in Rats, Pharmacology Biochemistry and Behavior, 48(1):193-201.

Jain et al. (Oct. 2002) Bupropion SR vs. Placebo for Weight Loss in Obese Patients with Depressive Symptoms, Obesity Research, 10:1049-56.

Jallon et al. (2001) Bodyweight gain and anticonvulsants: a comparative review. Drug Safety; 24(13):969-978.

Janssen et al., 1999, Effects of sex on the change in visceral, subcutaneous adipose tissue and skeletal muscle in response to weight loss, International Journal of Obesity, 23, pp. 1035-1046.

Japanese Journal of Clinical Psychiatry (1987 16(1):123-132), and English-language version of Japanese Office Action citing the same (dated Oct. 28, 2008).

Jones et al., 2003, Effect of naltrexone on food intake and body weight in Syrian hamsters depends on metabolic status, Physiology & Behavior 28:67-72.

Kanba et al. (1994) The first open study of zonisamide, a novel anticonvulsant, shows efficacy in mania. Progress in Neuro-Psychopharmacology and Biological Psychiatry; 18(4):707-715.

Kelly et al., 2006, Adjunct divalproex or lithium to clozapine in treatment-resistant schizophrenia, Psychiatric Quarterly, 77(1):81-94.

Kim et al. 1990. Open fixed dose trial of fluoxetine in the treatment of obsessive compulsive disorder. Drug Development Research, 19:315-319.

Kimura et al., 1992, Pharmacokinetic interaction of zonisamide in rats: effects of other antiepileptics on zonisamide, J. Pharmacobio-Dyn. 15:631-639.

Kiptoo et al. (2006) Enhancement of Transdermal delivery or 6-B-naltrexol via a codrug linked to hydroxyburpropion, Journal of Controlled Release 113:137-145.

Kirkham et al. (2001) Synergistic effects of opioid and cannabinoid antagonists on food intake. Psychopharmacology; 153:267-270.

Kirov et al. (2003) Add-on topiramate reduces weight in overweight patients with affective disorders: a clinical case. BMC Psychiatry, 5:19, 8 pp.

Klok et al., 2002, Cholesteryl-(l-lactic acid)n building blocks for self-assembling biomaterials, Macromolecules, 35:746-759.

Kolb et al. (1985) Synthesis and Pharmacological Characterization of Fluorescent Opioid Receptor Probes. A. Pharmaceutical Res, 2(6):266-271.

Korner et al. (2003) The emerging science of body weight regulation and its impact on obesity treatment, J. Clin. Invest. 111(5):565-570.

Kossard, et al. 2006. Defining urticarial dermatitis: A subset of dermal hypersensitivity reaction pattern. Arch. Dermatol., 142:29-34.

Krauss et al. 1997. Tics secondary to craniocerebral trauma, Movement Disorders, 12(5):776-782.

Kristeller et al., Jan. 12, 1999, An exploratory study of a meditation-based intervention for binge eating disorder, J. Health Psychol, 4(3):357-363.

Krupitsky et al. 2006. Naltrexone with or without fluoxetine for preventing relapse to heroin addiction in St. Petersburg, Russia. Journal of Substance Abuse Treatment, 31:319-328.

Kuk et al., 2006, Visceral fat is an independent predictor of all-cause mortality in men, Obesity, 14(2):336-341.

Kushner et al. (Mar. 2002) Obesity pharmacology: past, present, and future, Current Opinion in Gastroenterology, pp. 213-220.

Landabaso et al. 1998. A randomized trial of adding fluoxetine to a naltrexone treatment programme for heroin addicts. Addiction, 93(5):739-744.

Le Bourdonnec et al., 2002, Reporter affinity labels: an o-phthalaldehyde derivative of β-naltrexamine as a fluorogenic ligand for opioid receptors, J. Med. Chem., 43(13):2489-2492.

Leppik (Dec. 2004) Zonisamide: chemistry, mechanism of action, and pharmacokinetics, Seizure, 13(Suppl 1):S5-9; discussion S10.

Leppik et al. (1993) Efficacy and safety of zonisamide: results of a multicenter study. Epilepsy Research; 14:165-173.

Lesch et al. 1991. Long-term fluoxetine treatment decreases 5-HT1A receptor responsivity in obsessive-compulsive disorder. Psychopharmacology, 105:415-420.

Lessig et al. (Dec. 2001) Topiramate for Reversing Atypical Antipsychotic Weight Gain, J. Am. Child Adolesc. Psychiatry 40(12):1364.

Levy et al. (Nov. 2002) Topiramate Produced Weight Loss Following Olanzapine-Induced Weight Gain in Schizophrenia, J. Clin. Psychiatry, 63(11):1045.

Levy et al. 1985. Utility of free level monitoring of antiepileptic drugs. Epilepsia, 26(3):199-205.

Lin et al. 2000. Development of high fat diet-induced obesity and leptin resistance in C57B1/6J mice. International Journal of Obesity, 24:639-646.

López-Ibor, Jr. et al. 1996. Double-blind comparison of fluoxetine versus clomipramine in the treatment of obsessive compulsive disorder. European Neuropsychopharmacology, 6:111-118.

Lowry, Feb. 2008, Study: bupropion-naltrexone combo best for weight loss, Clinical Psychiatric News, 1 pp.

Malcolm et al. (Jun. 1985) A Controlled Trial of Naltrexone in Obese Humans, International Journal of Obesity, 9:347-353.

Malhotra et al. (2002) Medical Management of Obesity Associated With Mental Disorders, Journal of Clinical Psychiatry, 63(suppl 4):24-32.

Matsuura (2000) Indication for Anterior Temporal Lobectomy in Patients with Temporal Lobe Epilepsy and Psychopathology, Epilepsia, 41(Suppl. 9):39-42.

McDougle et al. (Aug. 2000) A double-blind, placebo-controlled study of risperidone addition in serotonin reuptake inhibitor-refractory obsessive-compulsive disorder, Archive of General Psychiatry, 57(8):794-801.

(56) References Cited

OTHER PUBLICATIONS

McElroy et al. (2000) Pharmacologic agents for the treatment of acute bipolar mania, Biological Psychiatry, 48(6):539-557.
McElroy et al. (2004) Zonisamide in the Treatment of Binge-Eating Disorder: An Open-Label, Prospective Trial, J. Clin. Psychiatry, 65(1):50-56.
McElroy et al. (2004) Zonisamide is effective in the treatment of binge-eating disorder. Inpharma; 1428:10.
McLaughlin et al. (2003) The cannabinoid CB1 antagonists SR 141716A and AM 251 suppress food intake and food-reinforced behavior in a variety of tasks in rats. Behavioral Pharmacology; 14:583:588.
Michelson et al. (Nov. 2001) Atomexetine in the Treatment of Children and Adolescents with Attention Deficit/Hyperactivity Disorder: A Randomized, Placebo-Controlled, Dose-Response Study, Pediatrics, 108(5):E83 Abstract.
Millet et al. 1999. Obsessive-compulsive disorder: Evaluation of clinical and biological circadian parameters during fluoxetine treatment. Psychopharmacology, 146:268-274.
Mitchell et al. (1987) High-Dose Naltrexone Therapy and Dietary Counseling for Obesity, Biological Psychiatry, 22:35-42.
Monteleone et al. 1995. Plasma melatonin and cortisol cirdadian patterns in patients with obsessive-compulsive disorder before and after fluoxetine treatment. Psychoneuroendocrinology, 20(7):763-770.
Morris, III (Dec. 3, 2000) The Effect of Zonisamide Administration on Patient Weight, A Scientific Exhibit at the American Epilepsy Society Annual Meeting, Los Angeles, California.
Must et al. (Oct. 27, 1999) The disease burden associated with overweight and obesity, JAMA, 282(16):1523-1529.
Najim et al., Dec. 1, 1993, Role of endorphins in benzodiazepine-induced hyperglycaemia in mice, Pharmacology Biochemistry and Behavior, 46(4):995-997.
Naltrexone (Oral Route), MayoClinic.com, 11 pp., 2009.
Nash et al., Jul. 1, 2004, Anxiety disorders, Medicine, 32(7):17-21.
National Institutes of Health, Apr. 18, 2008, Efficacy and safety study of combination therapy to treat uncomplicated obesity, http://clinicaltrials.gov/show/NCT00364871, 5 pp.
Navarro et al. (Jun. 2001) Topiramate for Clozapine-Induced Seizures, Am. J. Psychiatry, 158(6):968-969.
NDA 20-711, Approval Letter of Application No. NDA 20-711, Department of Health and Human Services, May 14, 1997, 4 pp.
NDA 20-789/S-005 Zonegran (zonisamide) Capsules 100 mg, FDA Approved Labeling Text dated Oct. 7, 2002, 2 pp.
NDA 20-789, Zonegran (zonisamide) Capsules 100 mg, FDA Approved Labeling Text, p. 1-24 (Mar. 27, 2000).
Neumeister et al. 1999. Addition of naltrexone to fluoxetine in the treatment of binge eating disorder. Am. J. Psychiatry, 156(5):797.
NIH Publication No. 05-3892, Dec. 2004, National Diabetes Statistics, 18 pp.
Ninan et al., 1992, An improved synthesis of noroxymorphont, Tetrahedron., 48(32):6709-6716.
Niswender et al. 1997. Effects of increased glucokinase gene copy number on glucose homeostatis and hepatic glucose metabolism. The Journal of Biological Chemistry, 272(36):22570-22575.
Note for guidance on stability testing of existing active substances and related finished product, Committee for Proprietary Medicinal Products (CPMP), Apr. 22, 1998, 9 pp.
Novi et al. (Apr.-Jun. 1990) The role of oploid antagonists in the treatment of obesity. Results of a clinical trial with naltrexone, Minerva Endocrinol. 15(2):121-3, Abstract.
O'Byrne et al., Jan. 1, 1990, Effects of drugs on glucose tolerance in non-insulin-dependent diabetes (part II), Drugs, Adis International Ltd., 40(2):204-219.
Okada et al. (1992) Effects of zonisamide on extracellular levels of monoamine and its metabolite, and on Ca2+ dependent dopamine release Epilepsy Research, 13:113-119.
Okada et al. (1995) Effects of zonisamide on dopaminergic system, Epilepsy Research, 22:198-205.
Olsen et al., (1990) Conjugate Addition Ligands of Opioid Antagonists. Methacrylate Esters and Ethers of 6Alpha- and 6Beta-Naltrexol, Journal of Medicinal Chemistry, American Chemical Society, 33(2):737-741.
Olszewski et al. (Jun. 13, 2001) Evidence of Interactions Between Melanocortin and Opioid Systems in Regulation of Feeding, NeuroReport, 12(8):1727-1730.
Oommen et al. (1999) Zonisamide: A new antiepileptic drug. Clinical Neuropharmacology, 22(4):192200.
Ortho-Novum Tablets and Modicon Tablets Prescribing Information, Apr. 2002, 8 pp.
Otake et al. (May 15, 2005) Association of visceral fat accumulation and plasma adiponectin and colorectal ademona: evidence for participation of insulin resistance, Clinical Cancer Research 11:3642-3646.
Ovadia, Oct. 1999, A Novel Twist on Binge Eating Treatment, Psychiatric Dispatches in Primary Psychiatry; 6(10):24-29.
Paar et al., 2002, Bivalent ligands with rigid double-stranded DNA spacers reveal structural constraints on signaling by FceRI, J. Immunol., 169:856-864.
Paile-Hyvarinen et al., Mar. 14, 2003, Quality of life and metabolic status in mildly depressed women with type 2 diabetes treated with paroxetine: a single blind randomised placebo controlled trial, BMC Family Practice, Biomed Central, 4(1), 6 pp.
Pasternak et al. (1980) Long-acting opiate agonists and antagonists: 14-hydroxydihydromorphinone hydrazones, Med. Chem, 23:674-676.
Pavuluri et al. (2002) Topiramate Plus Risperidone for Controlling Weight Gain and Symptoms in Preschool Mania, Journal of Child and Adolescent Psychopharmacology, 12(3):271-273.
Penn et al., 2003, Pharmacotherapy of obesity in the near term, Current Opinion in Endocrinology and Diabetes, 18(2):311-316.
Portoghese et al., 1982, Opioid agonist and antagonist bivalent ligands as receptor probes, Life Sciences, 31:1283-1286.
Portoghese et al., 1986, Opioid agonist and antagonist bivalent ligands. The relationship between spacer length and selectivity at multiple opioid receptors, J. Med. Chem., 29:1855-1861.
Portoghese et al., 1986, Synthesis and Opioid antagonist potencies of naltrexamine bivalent ligands with conformationally restricted spacers J. Med. Chem., 29:1650-1653.
Portoghese, 1992, The role of concepts in structure-activity relationship studies of opioid ligands, J. Med. Chem., 35:1927-1937.
Potter et al., 1997, Sustained Weight Loss Associated with 12-month topiramate Therapy, Epilepsia, Raven Press Ltd. New York, 38(Suppl 8):97.
Rao et al. (1998) Fixed-does combination therapy: panacea or poison?, Intensive Care Med, 24:283-285.
Reaven, G. M. 1995. Pathophysiology of insulin resistance in human disease. Physiological Reviews, 75(3):473-486.
Reents et al. (1988) Nalozone and naltrexone, Chest, 93(1):217-219.
Remington's Pharmaceutical Sciences. 18th Edition; Easton, PA: Mack Publishing Co. (1990).
Reneric et al. (Nov. 1998) Opioid Receptor Antagonists in Psychiatry, CNS Drugs, 10(5):365-382.
Rezvani et al. 2000. Combination pharmacotherapy: A mixture of small doses of naltrexone, fluoxetine, and thyrotropin-releasing hormone analogue reduces alcohol intake in three strains of alcohol-preferring rats. Alcohol & Alcoholism, 35(1):76-83.
Romano et al. 2001. Long-term treatment of obsessive-compulsive disorder after an acute response: A comparison of fluoxetine versus placebo. Journal of Clinical Psychopharmacology, 21(1):46-52.
Rotzinger et al. (1999) Metabolism of some 'second' and 'fourth' generation antidepressants: iprindole, viloxazine, bupropion, mianserin, maprotiline, trazadone, nefazodone, and vaniafaxine, Cellular and Molecular Neurobiology, 19:430.
Rowland et al. (2001) Effects of the cannabinoid receptor antagonist SR 141716, alone and in combination with dexfenfluramine or naloxone, on food intake in rats. Psychopharmacology; 159:111-116.
Saba et al. 2002. Lamotrigine-clozapine combination in refractory schizophrenia: Three cases. The Journal of Neuropsychiatry and Clinical Neurosciences, 14(1):86.

(56) References Cited

OTHER PUBLICATIONS

Sackellares et al. (1985) Pilot study of zonisamide (1,2-benzisoxazole-3-methanesulfonamide) in patients with refractory partial seizures. Epilepsia, 26(3):206-211.
Saper et al. (2002) The need to feed: Homeostatic and hedonic control of eating, Neuron, 36:199-211.
Sashiwa et al., 2000, Chemical modification of chitosan. 3. Hyperbranched chitosan-sialic acid dendrimer hybrid with tetraethylene glycol spacer, Macromolecules, 33:6913-6915.
Sayre et al., 1984, Design and synthesis of naltrexone-derived affinity labels with nonequilibrium opioid agonist and antagonist activities. Evidence for the existence of different receptor subtypes in different tissues, J. Med. Chem., 27:1325-1335.
Scheen et al., May 1, 2005, Diabete sucre iatrogene: l'exemple des anti-phsychogiques atypiques, Revue Medicale de Liege, 60(5-6):455-460.
Schimmel et al., 1974, Inhibition by diphenylhydantoin of the diabetogenic action of streptozocin, Horm. Metab. Res. 6:475-477.
Schmidhammer et al. (1994) Mixed Azines of Naloxone with Dihydromorphinone Derivatives. A. Helv. Chim. Acta; 77:999-1002.
Schmidt et al. (1993) Zonisamide for add-on treatment of refractory partial epilepsy: a European double-blind trial. Epilepsy Research; 15:67-73.
Shapira et al. (2000) Treatment of Binge-Eating Disorder with Topiramate: A Clinical Case Series. J. Clin. Psychiatry; 61(5):368-371.
Shapira et al. 2004. A double-blind, placebo-controlled trial of olanzapine addition in fluoxetine-refractory obsessive-compulsive disorder. Biol. Psychiatry, 550:553-555.
Shapiro et al. (2005) Additive Benefits of Combination Therapy with Sibutramine and Rimonabant on Body Weight, Insulin Sensitivity and Lipoproteins in Diet-Induced Obese Mice, 2005 NAASO Annual Meeting, Poster 405-P.
Shelton (2003) Classification of Antidepressants and their Clinical Implications, Primary Care Companion J. Clin. Psychiatry, 5(Supp. 7):27-32.
Shriqui et al. (Jul. 2002) Atypical Antipsychotics, The Canadian Journal of CME, pp. 65-80.
Sitsen et al., 2001, Drug-drug interaction studies with mirtazapine and carbamazepine in healthy male subjects, European Journal of Drug Metabolism and Pharmacokinetics, 26(1-2):109-121.
Sleep Disorders, in Diagnostic and Statistical Manual of Mental Disorders, 4$^{th}$ Edition, American Psychiatric Association, pp. 583-595 (2000).
Sneer et al., Protective effect of diphenylhydantoin on the diabetes-inducing effect of alioxan, database accession No. 1980:34024.
Spigset et al. (2001) Therapeutic Approaches to Bulimia Nervosa, Expert Opinion on Therapeutic Patents, 11(3):463-477.
Srivastava et al. 1975. Organic disulfides and related substances. 38. Some disulfide and trisulfide sulfinate salts as antiradiation drugs. Journal of Medicinal Chemistry, 18(8):798-802.
Steffen et al. 2006. Emerging drugs for eating disorder treatment. Expert Opin. Emerging Drugs, 11(2):315-336.
Stein (Feb. 15, 2000) Neurobiology of the obsessive-compulsive spectrum disorders, Biological Psychiatry 47(4):296-304.
Stein (Aug. 3, 2002) Obsessive-compulsive disorder, Lancet 360(9330):397-405.
Stepinski et al., 1991, Use of hydrophilic diamines for bridging of two opioid peptide pharmacophores, Internat. J. of Peptide & Protein Res., 38:588-592.
Storch et al. 2006. Clinical predictors of early fluoxetine treatment response in obsessive-compulsive disorder. Depression and Anxiety, 23:429-433.
Stromberg et al. (2002) A comparison of the effects of 6-beta naltrexol and naltrexone on the consumption of ethanol or sucrose using a limited-access procedure in rats. Pharmacology, Biochemistry, and Behavior, 72:483-490.
Swedo et al. 1998. Pediatric autoimmune neuropsychiatric disorders associated with streptococcal infections: Clinical description of the first 50 cases. Am. J. Psychiatry, 155(2):264-271.
Symons et al. 2004. Self-injurious behavior and the efficacy of naltrexone treatment: A quantitative synthesis. Mental Retardation and Developmental Disabilities Research Reviews, 10:193-200.
Tamiz et al., 2000, Application of the bivalent ligand approach to the design of novel dimeric serotonin reuptake inhibitors, J. Am. Chem. Soc., 122:5393-5394.
Tamiz et al., 2001, Pharmacological and behavioral analysis of the effects of some bivalent ligand-based monoamine reuptake inhibitors, J. Med. Chem., 44:1615-1622.
Tavakoli et al., Jul. 2003, Diabetic ketoacidosis in a patient with olanzapine, valproic acid, and venlafaxine, Southern Medical Journal, 96(7):729-730.
Testa, 2004, Prodrug research: futile or fertile?, Biochemical Pharmacology, 68:2097-2106.
Thearle et al. (2003) Obesity and Pharmacology, Endocrinology and Metabolism Clinics of North American, W.B. Suanders Company, Philadelphia US 32(4):1005-1024.
Thombre et al. (2004) Osmotic drug delivery using swellable-core technology, Journal of Controlled Release 94:75-89.
Tollefson et al. (1997) Olanzapine versus haloperidol in the treatment of schizophrenia and schizoaffective and schizophreniform disorders: results of an international collaborative trial, Am J. Psychiatry, 154(5):457-465.
Turnbull et al., Jan. 1985, The effect of valproate on blood metabolite concentrations in spontaneously diabetic, ketoacidotic, bb/e wistar rats, Diabetes Research 2(1):45-48.
Tutka et al., 2004, Convulsant and anticonvulsant effects of bupropion in mice, European Journal of Pharmacology, 499:117-120.
Van Schaftingen et al. (1992) The regulatory protein of liver glucokinase. Advan. Enzyme Regul., 32:133-148.
Vieta et al. (2003) 1-year follow-up of patients treated with risperidone and topiramate for a manic episode, J Clin Psychiatry, 64(7):834-829.
Vieta et al. (2004) Effects on weight and outcome of long-term olanzapine-topiramate combination treatment in bipolar disorder. Journal of Clinical Psychopharmacology 24(4):374-378.
Vythilingum et al. 2005. Obsessive-compulsive disorders and dermatologic disease. Dermatologic Clinics, 23:675-680.
Wadden et al. (2000) Effects of Sibutramine Plus Orlistat in Obese Women Following 1 Year of Treatment by Sibutramine Alone: A Placebo-Controlled Trial, Obesity Research; 8(6):431.
Wadden et al., Jan. 2011, Weight loss with naltrexone SR/bupropion SR combination therapy as an adjunct to behavior modification: the COR-BMOD trial, Obesity, 19(1):110-120.
Walker et al. (1988) Chronic Toxicity of the Anticonvulsant Zonisamide in Beagle Dogs, Fundamental and Applied Toxicology 11:333-342.
Wang et al. (2002) Gabapentin augmentation therapy in bipolar depression, Bipolar Disorders 4:296301.
Weintraub et al. (1992) Long-term Weight Control Study I (weeks 0 to 34) 'The Enhancement of Behavior Modification, Caloric Restriction, and Exercise by Fenfluramine Plus Phentermine versus Placebo', Clinical Pharmacology & Therapeutics, 51(5):586-94.
Welty et al. (Nov. 30-Dec. 5, 2001) Weight Loss Associated With Use of Zonisamide in European and US Clinical Trials, A Compendium of Posters and Platform Sessions for Zonegran®, Presented at the Annual Meeting 2001 of the American Epilepsy Society, Philadelphia, Pennsylvania.
Wermuth, Apr. 2006, Similarity in drugs: reflections on analogue design, Drug Discovery Today, 11(7/8):348-354.
Werneke et al. (2002) Options for Pharmacological Management of Obesity in patients Treated with Atypical Antipsychotics, International Clinical Psychopharmacology, 17(4):145-160.
Wheatley et al., 1998, Mirtazapine: efficacy and tolerability in comparison with fluoxetine in patients with moderate to severe major depressive disorder, J. Clin Psychiatry, 59(6):306-312, Abstract.
White et al. 2002. Development and validation of the food-craving inventory. Obesity Research, 10(2):107-114.
Wieczorek et al., 2001, The effects of the selective serotonin reuptake-inhibitor fluvoxamine on body weight in Zucker rats are mediated by cortocotrophin-releasing hormone, International Journal of Obesity, 25(10):1566-1569.

(56) References Cited

OTHER PUBLICATIONS

Wilcox et al., 2009, An open-label study of naltrexone and bupropion combination therapy for smoking cessation in overweight and obese subjects, Addictive Behaviors, 35(3):229-234.
Wilding (2004) Clinical evaluation of anti-obesity drugs. Current Drug Targets; 5:325-332.
Willmore, L. J. 2004. Commentary on Leppik. Seizure, 13S:S10.
Wilner, 2002, Is Weight Loss With Zonisamide Gender-Specific?, Annual Meeting of the American Epilepsy Society, https://secure.neurohub.net/cgi-perl/get.cgi?pub=52318&ext=htm, 1 pp.
Wolff (1995) Burger's Medicinal Chemistry and Drug Discovery, John Wiley & Sons, 5th Ed. 1:975-977.
Yeomans et al. (2002) Opioid peptides and the control of human ingestive behaviour, Neuroscience and Biobehavioral Reviews, 26:712-728.
Yoshimasu et al. (2003) Psychotropic Drug-Induced Obesity, Nippon Rinsho, 61(Suppl. 6):825-829. (English translation of Japanese Office Action containing Examiner's characterization of reference is appended to reference: Notice of Reasons for Rejection, Application No. 2006-549530).
Yu et al. (2005) Influence of insulin treatment on insulin sensitivity in insulin requiring type 2 diabetes patents, Diabetes Research and Clinical Practice, 68S1:S54-S59.
Zeng et al., 1988, Convenient synthesis of 9-alkyl and 9-arylacridines from [2-(trimethylsilyl)ethoxy]methyl (sem) protected acridone, Tetrahedron Letters, 29(40):5123-5124.
Zhang et al. (1994) Positional Cloning of the Mouse obese gen and its humane homologue, Nature, 372:425-432.
Zhu et al. (Apr. 3, 2002) Pharmacologic Treatment of Eating Disorders, Canadian Journal of Psychiatry, 47(3):227-234.
Zitterl et al. 1999. Efficacy of fluoxetine in Austrian patients with obsessive-compulsive disorder. Wiener Klinische Wochenschrift, 111(11):439-442.
Zohar et al. 1987. Serotonergic responsivity in obsessive-compulsive disorder. Arch. Gen. Psychiatry, 44:946-951.
Zonisamide (Oral Route), MayoClinic.com, 12 pp., 2009.
ISR and WO for PCT/US07/084178, dated Jul. 25, 2008.
IPRP for PCT/US07/084178, dated May 22, 2009.
Adis Data Information BV, 2010, Naltrexone/Bupropion Contrave ®; Naltrexone SR/Bupropion SR, Adis R&D Profile, 10(1):25-32.
Alger et al., Apr. 1991, Effect of a tricyclic antidepressant and opiate antagonist on binge-eating behavior in normoweight bulimic and obese, bing-eating subjects, The American Journal of Clinical Nutrition, 53(4):865-871.
Atlantis et al., Oct. 6, 2009, Obesity and depression or anxiety, BMJ 2009:339:B3868.
Campana et al., Jan. 2005, P.6.034 Naltrexone and cravings: does it work with eating disorders?, European Neuropsychopharmacology, 15:S283.
Carter et al. 2003. Pharmacologic treatment of binge-eating disorder, The International Journal of Eating Disorders, 34(Suppl):S74-S85.
Casado et al., Apr. 2003, Sibutramine decreases body weight gain and increases energy expenditure in obese Zucker rats without changes in NPY and orexins, Nutr Neurosci, 6(2):103-111 (abstract).
ClinicalTrials.gov archive, Apr. 21, 2008, A phase 3 study comparing the safety and efficacy of naltrexone sr/bupropion sr and placebo in obese subjects with type 2 diabetes mellitus, 3 pp.
ClinicalTrials.gov archive, May 2012, Cardiovascular outcomes study of Naltrexone SR/Bupropion SR in overweight and obese subjects with cardiovascular risk factors (the light study), 4 pp.
Cunningham, May 1963, Diethylpropion in the treatment of obesity, The Journal of the College of General Practitioner, 6(2):347-349.
Fujioka et al., Jan. 1987, Contribution of intra-abdominal fat accumulation to the impairment of glucose and lipid metabolism in human obesity, Metabolism, 36(1):54-59.
Gormally et al., 1982, The assessment of binge eating severity among obese persons, Addict Behav, 7(1):47-55.

Greenway et al., Oct. 22, 2010, Effect of naltrexone plus bupropion on weight loss in overweight and obese adults (COR-I): a multicentre, randomized, double-blind, placebo-controlled, phase 3 trial, Lancet, 376:595-605.
Horne et al., Jul. 1988, Treatment of bulimia with bupropion: a multicenter controlled trial, The Journal of Clinical Psychiatry, 49(7):262-266.
Housenloy, 2009, Contrave™: Novel treatment for obesity, Future Lipidology, 4(3):279-285.
Johnson et al., Oct. 14, 2010, Food effects on the pharmacokinetics of morphine sulfate and naltrexone hydrochloride extended release capsules, Advances in Therapy, 27(11):846-858.
Jonas et al.., 1986, Treatment of binge-eating an open-study of naltrexone, Society for Neuroscience Abstracts, 12(1):595.
Kennett et al., Nov. 2010, New approaches to the pharmacological treatment of obesity: can they break through the efficacy barrier?, Pharmacology Biochemistry and Behavior, 97(1):63-83.
Khaylis et al., Nov. 2010, A review of efficacious technology-based weight-loss interventions: five key components, Telemedicine and e-Health, 16(9):931-938.
Kivimaki et al., Common mental disorder and obesity—insight from four repeat measures over 19 years: prospective Whitehall II cohort study, BMJ 2009; 339:b3765.
Kodachi, Takehiko, Apr. 10, 1987, Introduction to modern pharmaceutics (3rd revised edition), 9.3 Sustainment of pharamacological action, Nankodo Co., Ltd, pp. 262-268.
Luppino et al., Mar. 2010, Overweight, obesity, and depression: a systematic review and meta-analysis analysis of longitudinal studies, Arch Gen Psychiatry, 67(3):220-229.
Marrazzi et al., Feb. 1995, Binge eating disorder: response to naltrexone, International Journal of Obesity, 19(2):143-145.
McLaughlin et al., 1983, Nalmefene decreases meal size, food and water intake and weight gain in Zucker rats, Pharmacology Biochemistry and Behavior, 19(2):235-240 (abstract).
Meyer, Dec. 2008, Alleviation of both binge eating and sexual dysfunction with naltrexone, Journal of Clinical Psychopharmacology, 28(6):722-723.
Midha et al., May 2005, Exposure measures applied to the bioequivalence of two sustained release formulations of bupropion, International Journal of Clinical Pharmacology and Therapeutics, 43(5):244-254.
Padwal, Oct. 6, 2009, Contrave, a bupropion and naltrexone combination therapy for the potential treatment of obesity, Curr. Opin. Investig. Drugs, 10(10):1117-1125 (abstract).
Pandit, 2007, Introduction to the Pharmaceutical Sciences, 1st Ed., Lippincott Williams & Wilkins, Baltimore, MD, p. 154.
Shuman et al., Jun. 1986, Abnormal body fat distribution detected by computed tomography in diabetic men, Investigative Radiology, 21(6):483-487.
Stansfeld et al., Aug. 1992, Social class and minor psychiatric disorder in British civil servants: a validated screening survey using the General Health Questionnaire, Psychological Medicine, 22:739-749.
Van Gaal et al., Aug. 1998, Sibutramine and fat distribution: is there a role for pharmacotherapy in abdominal/visceral fat reduction?, Int J Obes Relat Metab Disord, Suppl 1:S38-40; discussion S41-2 (abstract).
Altomonte et al., 1988, Effect of fenfluramine on insulin/growth hormone ratio in obese subjects, Pharmacology, 36(2):106-111.
Bengtsson, 1993, The consequences of growth hormone deficiency in adults, Acta Endocrinol. (Copenh.), 128(Suppl 2):2-5.
Brown et al., 2012, Current and emerging directions in the treatment of eating disorders, Substance Abuse: Research and Treatment, 6:33-61.
Brunk, Sep. 1, 2009, Significant weight loss shown with naltrexone/bupropion combo, Thoracic Surgery News, http://www.thoracicsurgerynews.com/?id=959378,tx_ttnews[tt_news]=86987&cHash=a97b7f3c0f6a8c6a3b3ca96df9a6b73f, 1 pp.
Carson et al., May 1996, Pilot study of the use of naltrexone to treat the severe pruritis of cholestatic liver disease, Amer. J. Gastroenterology, 91(5):1022-1023.
Chakraborty et al., 2010, Management of anorexia and bulimia nervosa: an evidence-based review, Indian J Psychiatry, 52:174-186.

(56) References Cited

OTHER PUBLICATIONS

Clinical Trials.gov, A Multicenter, randomized, double-blind, placebo-controlled study assessing the occurrence of major adverse cardiovascular events (MACE) such as cardiovascular death, non-fatal myocardial infarction, and non-fatal stroke in overweight and obese subjects who are at a higher risk of having these events because they ahv diabetes and/or other cardiovascular risk factors, NTC01601704, May 7, 2013, 4 pp.
Clinical Trials.gov, Jul. 13, 2009, An open-label study assessing the safety and efficacy of naltrexone sustained release (SR)/bupropion sustained release (SR) in overweight or obese subjects with major depression, 2 pp.
Das et al., 2003, Controlled-release of oral dosage forms, Formulation, Fill & Finish, pp. 10-16.
De Boer et al., 1995, Clinical aspects of growth hormone deficiency in adults, Endocrine Reviews, 16(1):63-86.
Eid et al., 2005, Effective treatment of polycystic ovarian syndrome with roux-en-y gastric bypass, Surgery for Obesity and Related Diseases, 1:77-80.
Ghisoli et al., 1980, Effects of dopaminergic receptor stimulation and opioid receptor blockade on GH incretion: preliminary findings, Boll. Soc. Ital. Biol. Sper., 56(12):1222-1225.
Ghisoli et al., 1980, Effects of interaction between 2-Br-α-ergocryptine (CB 154) and naloxone on the control of insulin secretion in normal man, Boll. Soc. Ital. Biol. Sper., 56(12):1215-1221.
Glod et al., Jul.-Sep. 2003, Open trial of bupropion sr in adolescent major depression, J Child Adolesc Psychiatr Nurs, 16(3):123-130.
Goodman & Gillman's, The Pharmacological Basis of Therapeutics, $19^{th}$ Ed., Edited by J. Hardman and L. Limbird, 2001, p. 6.
Gudmundur et al., 1997, Growth hormone treatment of abdominally obese men reduces abdominal fat mass, improves glucose and lipoprotein metabolism, and reduces diastolic blood pressure, J. Clin. Endocrin. and Metab., 82(3):727-734.
Guidance for Industry Estimating the Maximum Safe Starting Dose in Initial Clinical Trials for Therapeutics in Adult Healthy Volunteers, U.S. Department of Health and Human Services, U.S. Food and Drug Administration Center for Drug Evaluation and Research (CDER), Pharmacology and Toxicology, Jul. 2005.
Herper, Mar. 5, 2015, Top FDA Official Says Orexigen Study Result 'Unreliable', Misleading, http://www/forbes.com/sites/matthewherper/, 4 pp.
Hollander et al., Oct. 21, 2013, Effects of naltrexone sustained-release/bupropion sustained release combination therapy on body weight and glycemic parameters in overweight and obese patents with type 2 diabetes, Diabetes Care, 36(12):4022-4029.
Husten, Mar. 3, 2015, Orexigen Released Interim Data Without Approval of Trial Leaders, http://ww/forbes.com/sites/harryhusten, 6 pp.
Laessle et al., May 1997, A comparison of resting metabolic rate, self-rated food intake, growth hormone, and insulin levels in obese and nonobese preadolescents, Physiol. Behav., 61(5):725-729.
McElroy et al., May 7, 2012, Pharmacological management of binge-eating disorder: current and emerging treatment options, Therapeutics and Clinical Risk Management, 8:219-241.
Meyer et al., Sep. 1984, Bioequivalence, dose-proportionality, and pharmacokinetics of naltrexone after oral administration, J. Clin. Psychiatry, 45(9)(Sec. 2):15-19.
Milano et al., May-Jun. 2005, Treatment of bulimia nervosa with fluvoxamine: a randomized controlled trial, Advances in Therapy, 22(3):278-283.
Oncken et al., 2001, Adverse effects of Oral naltrexone: an analysis of data from two clinical trials, Psychopharmacology, 154:397-402.
Patel et al., Jun. 2011, A hospital-based observational study of type 2 diabetic subjects from Gujarat, India, Journal of Health, Population and Nutrition, 29(3):265-272.
Pearlstein et al., 2003, A double-blind, placebo-controlled trial of fluvoxamine in binge eating disorder; a high placebo response, Arch Womens Ment Health, 6:147-151.
Ramlo-Halsted et al., 2000, The natural history of type 2 diabetes: practical points to consider in developing prevention and treatment strategies, Clin. Diabetes, 18(2).
Rao, Mar. 2001, Insulin resistance syndrome, American Family Physician, 63(6):1159-1163.
Remington's Pharmaceutical Sciences, 1980, $16^{th}$ ed., Mack Publishing Company, Arthur Osol. Editor, pp. 1553-1594.
Remington's Pharmaceutical Sciences, 1980, $16^{th}$ ed., Mack Publishing Company, Arthur Osol. Editor, pp. 1592-1597.
Ricca et al., 2001, Fluoxetine and fluvoxamine combined with individaul congitive-behavior therapy in binge-eating disorder: a one-year follow-up study, Psychotherapy and Psychosomatics, 70:298-306.
Richelsen et al., Feb. 1994, Growth hormone treatment of obese women for 5 wk: effect on body composition and adipose tissue LPL activity, Am J. Physiol., 266(2 Pt 1):11-16.
Stedman's Medical Dictionary, $28^{th}$ ed., Lippincott Williams & Wilkins, Philadelphia, 1999, pp. 490-491 and 1552.
Tallarida, 2001, Drug synergism: its detection and applications, J. Pharmacol. and Expt. Therap., 298(3):865-872.
Wellbutrin® (bupropion hydrochloride) tablets, in Physicians' Desk Reference, 49th edition, 1995, pp. 824-827, 150.
White et al., 2003, Clarifying the role of insulin in type 2 diabetes management, Clinical Diabetes, 21(1):14-21.
Wong et al., Aug. 2004, Starting insulin treatment in type 2 diabetes, Australian Prescriber, 27(4):93-96.
Cleveland Clinic Press Release: "Clinical Trial Testing Safety of Obesity Drug Contrave Halted; 50 Percent Interim Data Released by the Study's Executive Committee", May 12, 2015, retrieved from http://my.clevelandclinic.org/about-cleveland-clinic/newsroom/releases-videos-newsletters/2015-5-12-clinical-trial-testing-safety-of-obesity-drug-contrave-halted.
Orexigen Therapeutics Press Release: "Orexigen Therapeutics Provides Statement on Termination of the Light Study and Updates on Contrave Collaboration with Takeda Pharmaceuticals", May 12, 2015, retrieved from http://ir.orexigen.com/phoenix.zhtml?c=207034&p=irol-newsArticle_Print&ID=2047312.
Orexigen Therapeutics Press Release: "Takeda Pharmaceuticals and Orexigen Therapeutics Announce Termination of the Cardiovascular Outcomes Study (Light Study) of the Obesity Drug Contrave® (naltrexone HCI and bupropion HCI)", May 12, 2015, retrieved from http://ir.orexigen.com/phoenix.zhtml?c=207034&p=irol-newsArticle_Print&ID=2046959.
Herper, "Heart Benefit for Orexigen Drug Nearly Vanishes with New Data", Forbes, May 12, 2015, retrived from http://www.forbes.com/sites/matthewherper/2015/05/12/heart-benefit-for-orexigen-drug-nearly-vanishes-with-new-data/.
Herper, "A Top Cardiologist Says a Diet Drug Maker Misled Patients and Investors", Forbes, May 12, 2015, retrieved from http://www.forbes.com/sites/matthewherper/2015/05/12/a-top-cardiologist-says-a-diet-drug-maker-misled-patients-and-investors/#.
Mukherjee, "Update: Takeda threatens to break off Orexigen collab after Contrave data drama", BioPharmaDive, May 12, 2015, retrieved from http://www.biopharmadive.com/news/update-takeda-threatens-to-break-off-orexigen-collab-after-contrave-data-d/396940/.
A multicenter, randomized, double-blind, placebo-controlled study assessing the occurrence of major adverse cardiovascular events (MACE) in overweight and obese subjects with cardiovascular risk factors receiving naltrexone SR/bupropion SR, Adis Clinical Trials Insight (Nov. 15, 2011), 5 pp.
Bakris et al., 2002, Orlistat improves blood pressure and control in obese subjects with treated but inadequately controlled hypertension, Journal of Hypertension, 20(11):2257-2267.
Eckel et al., Apr. 16, 2005, The metabolic syndrome, The Lancet 365:1415-1428.
Ioannides-Demos et al., 2005, Pharmacotherapy for obesity, Drugs, 65(10):1391-1418.
Klein et al., Jun. 1, 2009, Naltrexone plus bupropion combination causes significant weight loss without worsening psychiatric symptoms, Diabetes, 58(Suppl. 1):A444.

(56) References Cited

OTHER PUBLICATIONS

Ludman et al., "Does depression reduce the effectiveness of behavioral weight loss treatment?" Behav Med. 2010; 35(4):126-134 (abstract).

McElroy et al., Jun. 2013, Naltrexone/bupropion combination therapy in overweight or obese patients with major depressive disorder: results of a pilot study, Prim Care Companion CNS Disord, 15(3), 17 pp.

McElroy et al., Jun. 1, 2010, An open-label study evaluating the naltrexone SR/bupropion SR combination therapy in overweight or obese subjects with major depression, Diabetes, 59(Suppl. 1):A483.

Orexigen Therapeutics, Inc., A safety and efficacy study comparing naltrexone SR/bupropion SR and placebo in obese type 2 diabetics, http://clinicaltrials.gov/ct2/show/NCT00474630, 4 pp.

Orexigen Therapeutics, Inc., Method-of-use study assessing the effect of naltrexone sustained release (SR)/bupropion SR on body weight and cardiovascular risk factors in overweight and obese subjects, http://clinicaltrials.gov/ct2/show/NCT01764386, 5 pp. Feb. 9, 2013.

Pagoto et al., Association of Major Depression and Binge Eating Disorder with Weight Loss in a Clinical Setting, Obesity, Nov. 2007; 15(11):2557-2559.

Plodkowski et al., 2009, Bupropion and naltrexone: a review of their use individually and in combination for the treatment of obesity, Expert Opin. Pharmacother. 10(6):1069-1081.

METHODS FOR ADMINISTERING WEIGHT LOSS MEDICATIONS

This application is a continuation of U.S. patent application Ser. No. 12/838,364 filed on Jul. 16, 2010, which is a continuation of U.S. patent application Ser. No. 11/937,367 filed on Nov. 8, 2007, now abandoned, which claims benefit of U.S. Provisional Application Ser. No. 60/865,159, filed Nov. 9, 2006, each of which is hereby incorporated by reference in its entirety.

BACKGROUND

1. Field of the Invention

This invention relates to methods for administering pharmaceutical compositions, preferably, but not limited to, compositions that are useful for affecting weight loss, suppressing appetite and/or treating obesity-related conditions in individuals.

2. Description of the Related Art

Obesity is a disorder characterized by the accumulation of excess fat in the body. Obesity has been recognized as one of the leading causes of disease and is emerging as a global problem. Increased instances of complications from obesity, such as hypertension, non-insulin-dependent diabetes mellitus, arteriosclerosis, dyslipidemia, certain forms of cancer, sleep apnea and osteoarthritis, have been related to increased instances of obesity in the general population.

Prior to 1994, obesity was generally considered a psychological problem. The discovery of the adipostatic hormone leptin in 1994 brought forth the realization that in certain cases, obesity may have a biochemical basis. The corollary to this realization was the idea that treatment of obesity may be achieved by chemical approaches. Since then, a number of such chemical treatments have entered the market.

Various methods of treating diseases or conditions, for example, obesity and related conditions, involve administering certain drugs or combinations thereof. For example, a number of references disclose the administration of certain weight loss formulations that include an anticonvulsant, an opioid antagonist and/or a norepinephrine reuptake inhibitor (NRI) to a patient in need thereof to affect weight loss. See, for example, U.S. Patent Application Publication Nos. 2004/0033965; 2004/0198668; 2004/0254208; 2005/0137144; 2005/0143322; 2005/0181070; 2005/0215552; 2005/0277579; 2006/0009514; 2006/0142290; 2006/0160750 and 2006/0079501, all of which are hereby incorporated by reference in their entireties.

However, the administration of certain pharmaceuticals, including but not limited to certain weight loss formulations, at a full dosage may initially incur adverse side effects, such that patients may be unable to tolerate a full dosage of the indicated medication. This intolerance may lead to more severe side effects and/or premature abandonment of the effective dosages and/or the treatment program. For example, administering an anticonvulsant in combination with an antidepressant may provide a combination having an enhanced ability to affect weight loss, but does not necessarily reduce or eliminate the initial adverse side effects that may accompany the administration of the anticonvulsant. Similarly, the administration of an opioid receptor antagonist in combination with an antidepressant may provide a combination having an enhanced ability to affect weight loss, but does not necessarily reduce or eliminate the adverse side effects that may accompany administration of the opioid antagonist.

SUMMARY

Methods and systems have now been developed for administering effective amounts of pharmaceutical formulations, preferably weight loss formulations, while reducing, minimizing and/or eliminating potential initial adverse side effects on the patient. In general terms, these methods and systems involve altering the dosage of one or more components of a multi-component formulation during the course of administration. For example, in an embodiment, the dose of one drug in a two-drug weight loss formulation is gradually increased from an initial low dose to an effective maintenance dose during subsequent administrations. In preferred embodiments, adverse side effects are reduced, and patient compliance and comfort are increased, thereby increasing the efficacy of the treatment regimen.

An embodiment provides a method of treating a disease or condition, for example, affecting weight loss, suppressing appetite and/or treating an obesity-related condition. The method comprises administering to a patient in need thereof a first dosage including a first drug and a second drug; and administering a second dosage comprising the first drug and the second drug, wherein the second dosage includes a different amount of the second drug than the first dosage.

Another embodiment provides a unit dosage package for a pharmaceutical composition. The unit dosage package comprises a first unit dosage including a first drug and a second drug; a second unit dosage comprising the first drug and the second drug, wherein the second unit dosage comprises a different amount of the second drug than the first unit dosage; and a unit dosage package configured to hold the first unit dosage and the second unit dosage.

Another embodiment provides a method of packaging a combination of bupropion and at least one of zonisamide and naltrexone. The method comprises providing a unit dosage package that holds the bupropion and the at least one of the zonisamide and the naltrexone; and packaging administration instructions with the unit dosage package in a unit dosage package.

These and other embodiments are described in greater detail below.

BRIEF DESCRIPTION OF THE DRAWINGS

These and other aspects of the embodiments will be readily apparent from the description below and the appended drawings, in which like reference numerals refer to similar parts throughout, which are meant to illustrate and not to limit the embodiments, and in which.

Figure 1A:
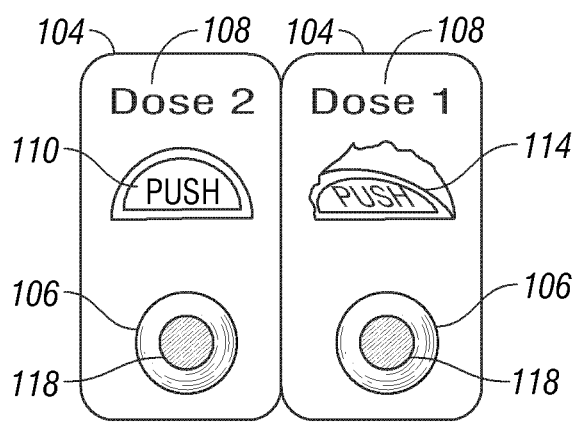
FIG. 1A is a front perspective of unit cells in an embodiment of a unit dosage package.

It will be understood that for the unit dosage packages described and/or depicted herein, rows (horizontal) and columns (vertical) may be inverted so that rows become columns and columns become rows. Such an inversion is within the scope of the present disclosure although as a convention this application generally refers to horizontal as rows and vertical as columns.

DETAILED DESCRIPTION OF THE PREFERRED EMBODIMENTS

The preferred embodiments described herein relate generally to systems and methods for administering pharmaceutical compounds for treatment of a disease or condition, (e.g., affecting weight loss, suppressing appetite and/or treating an obesity-related condition), while reducing, minimizing and/or eliminating potential initial adverse side effects on a patient. In general terms, these methods and systems involve altering the dosage of one or more ingredients of a multi-ingredient pharmaceutical formulation during the course of administration. For example, in an embodiment, the dose of one drug in a two-drug weight loss formulation is gradually increased from an initial low dose to an effective maintenance dose during subsequent administrations. In preferred embodiments, adverse side effects are reduced, patient compliance and comfort are increased, and thereby the efficacy of the treatment regimen is increased.

A pharmaceutical formulation comprises two or more pharmaceutical compositions administered either as discrete simultaneously administered dosages or as a single dosage form administration comprising two or more active ingredients or pharmaceutical compositions, e.g. a multilayer tablet. A pharmaceutical composition is a mixture of chemical compounds (e.g. one or more drugs) with additional pharmaceutical compounds, such as diluents or carriers. The pharmaceutical composition facilitates administration of the drug to an organism. Pharmaceutical compositions may be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid and the like. A "drug" as used herein refers both to active ingredients and formulations that have received FDA approval as well as those that have not received FDA approval.

In some embodiments a multilayer tablet is a pharmaceutical formulation comprising two or more pharmaceutical layers comprising pharmaceutical compositions and an intermediate layer between at least two of the two or more pharmaceutical layers. The intermediate layer is configured to dissolve in vivo with a substantially higher dissolution rate than at least two of the two or more pharmaceutical layers. Novel multilayer tablet formulations are described in co-pending application entitled LAYERED PHARMACEUTICAL FORMULATIONS, filed on the same date as the present application, which is hereby incorporated by reference in its entirety.

Methods of treating a disease or condition, preferably affecting weight loss, suppressing appetite and/or treating an obesity-related condition, as described herein, comprise administering a series of dosages to a patient. For example, administering a first dosage comprises administering a first drug and a second drug. Each drug may be administered separately or each drug may be part of a single dosage, e.g., a capsule or multilayer tablet. Multiple techniques of administering a drug exist in the art including, but not limited to, oral, injection, aerosol, parenteral and topical administration. Administration of a second dosage comprises administering the first drug and the second drug. The amount of the second drug in the second administration is different and, in a preferred embodiment, greater than the amount of the second drug in the first administration. In subsequent administrations, the amount of the second drug may be increased until an effective maintenance dose is reached.

Some drugs may incur initial and/or severe side effects when administered at an effective maintenance dose. Such drugs may be coupled with other drugs in pharmaceutical compositions to increase the efficacy or tolerability (e.g. by reducing adverse side effects) of one or both drugs. When such pharmaceutical formulations are administered according to the systems and methods described above, the side effects that might otherwise be present during administration are reduced or eliminated.

For example, some pharmaceutical formulations for affecting weight loss, suppressing appetite and/or treating an obesity-related condition while reducing, minimizing and/or eliminating potential initial adverse side effects on a patient include administration of an antidepressant in conjunction with an anticonvulsant and/or an opioid receptor antagonist. In a preferred embodiment, the pharmaceutical formulation comprising the antidepressant with the anticonvulsant or the opioid receptor antagonist is effective at treating obesity. A first dosage comprising the antidepressant with the anticonvulsant or the opioid receptor antagonist is administered on a first day. A second dosage comprising the antidepressant with the anticonvulsant or the opioid receptor antagonist is administered on a second day. The amount of the anticonvulsant or the opioid receptor antagonist in the second dosage is increased relative to the first dosage. In each subsequent dosage, an amount of the anticonvulsant or the opioid receptor antagonist is increased until a maintenance dosage is reached. In this manner, the patient may become accustomed to the administration of the dosage of the anticonvulsant or the opioid receptor antagonist present in the pharmaceutical formulation. The patient is then less likely to have initial and/or severe side effects that might otherwise accompany a dosage of the anticonvulsant or the opioid receptor antagonist with the antidepressant in an amount effective to treat obesity related conditions.

For practical purposes, in some embodiments unit dosage packages are employed to facilitate the methods described herein. Unit dosage packages comprise pharmaceutical formulations of drugs for treating a disease or condition, preferably for affecting weight loss, suppressing appetite and/or treating an obesity-related condition. Unit dosage packages comprise a first unit dosage comprising a first drug and a second drug, and a second unit dosage comprising the first drug and the second drug. In the second unit dosage, the amount of the second drug is different than the amount of the second drug in the first unit dosage.

FIG. 1A illustrates an embodiment of the unit dosage package. FIG. 1A shows a front side 100 of unit cells 104. Each unit cell 104 contains at least one blister 106 with a cavity that encloses a pharmaceutical composition 118. The unit cell 104 contains a label 108 for a specific dose (or instructions for administering a unit dosage) contained within the unit cell 104. The unit cell 104 also optionally comprises a closed push-through tab 110 and optionally a corresponding open push-through tab 114, which has been pushed from the front side 100 of the unit cell 104 to the back, to open the blister 106 and provide access to the pharmaceutical composition 118. In some embodiments, the tab is not present, and the dosage is pushed through the covering of the blister pack for dispensing.

Figure 1B:
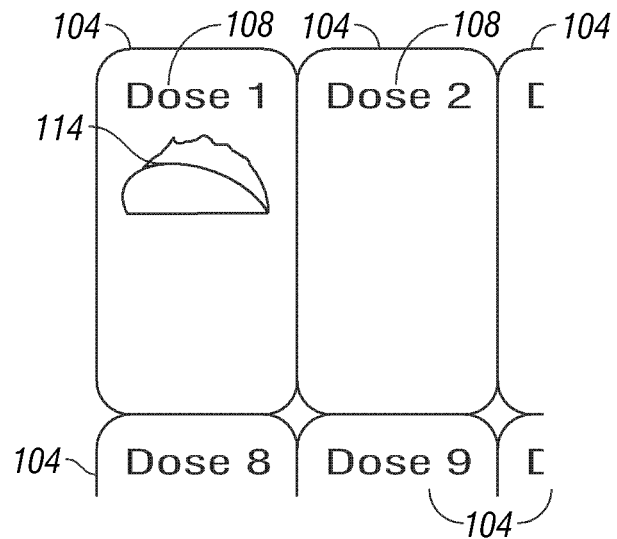
FIG. 1B is a back perspective of unit cells in an embodiment of a unit dosage package.

FIG. 1B shows a back side 102 of the unit dosage package. The unit cell 104 in this embodiment has a label 108 for a single dose contained within the unit cell 104, wherein the label 108 on the back side 102 corresponds to the label 108 on the front side of the unit dosage package 100. Shown in the embodiment of FIG. 1B is an open push-through tab 114 before it has been peeled back or removed to open the blister 106.

Figure 1C:
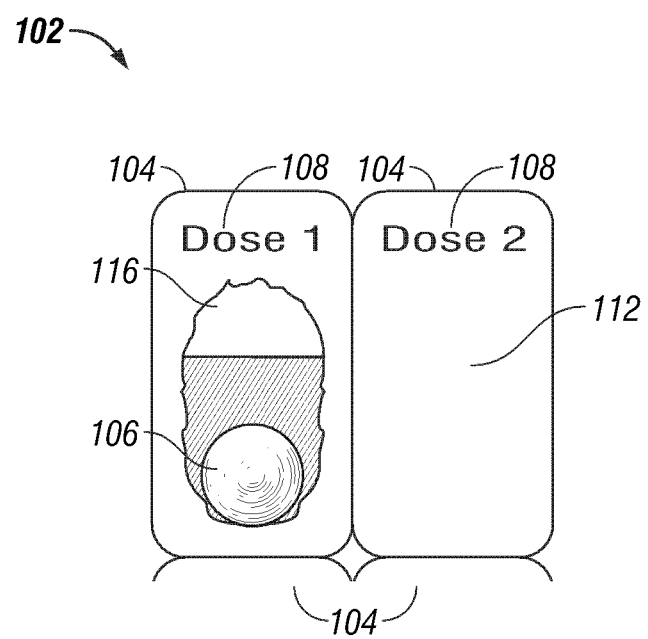
FIG. 1C is a back perspective of unit cells in an embodiment of a unit dosage package.

In FIG. 1C the back side 102 of the unit dosage package is illustrated with an unopened unit cell 112 contrasted with an opened and peeled back push-through tab 116 that allows dispensing of the pharmaceutical composition 118 from the blister 106.

Figure 2A:
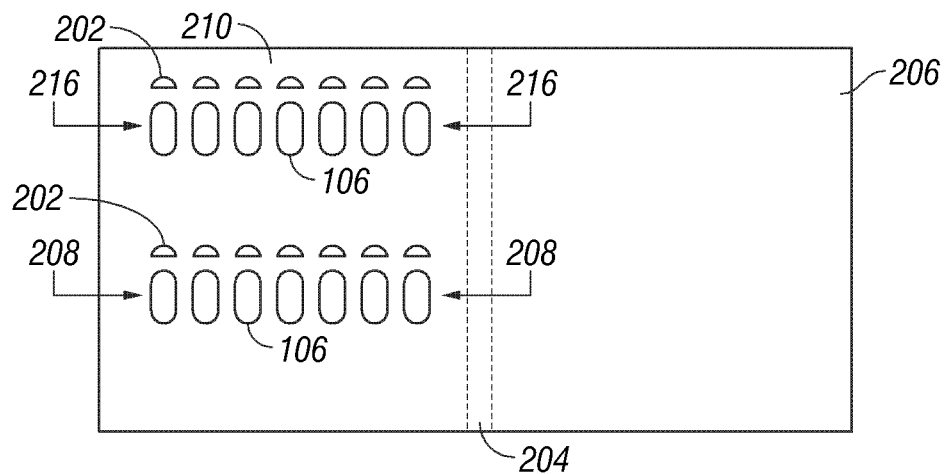
FIG. 2A is a front perspective view of an embodiment of a unit dosage package with two rows of unit cells.

In another embodiment, FIG. 2A is a front side of a unit dosage package 210 attached to a cover 206. The attached cover 206 folds to cover the front side of the unit dosage package 210 by means of a fold 204 which connects the cover 206 to the unit dosage package. The unit dosage package 210 contains at least one blister 106 with a cavity that protrudes through the front of the unit dosage package 210. In some embodiments the blisters 106 are thermo-formed or cold-formed blisters.

A plurality of the blisters on unit cells is formed into rows such as the row illustrated in FIG. 2A between the arrows 216 or the row between the arrows 208. A row of blisters 216 corresponds to increasing dosages of a specific pharmaceutical ingredient or composition. In one embodiment a single blister 106 within a row contains a dosage combination of an anticonvulsant and an antidepressant. The amount of the anticonvulsant increases in each dosage from one end of the row 208 to an opposite end, while the amount of antidepressant is constant in every dosage contained in the row 208.

Optionally, push-through tabs 202 allow for the opening of a single blister 106 in either the row 216 or the row 208. For example, the push-through tab 202 allows for opening the blister 106 by pushing the tab 202 from the front of the unit dosage package 210 through the back of the unit dosage package using a key, a pen, a pin, a thumbnail or some other object. The unit dosage package is then turned over and the push-through tab 202 is peeled away to expose and/or remove the unit dosage package backing. A dosage otherwise contained within a blister 106 may then be pushed through the backing and out of the back of the unit dosage package. Alternatively, the dosage is pushed through the backing without the optional tab. One of skill in the art will appreciate that the blisters can be on the top or bottom, and the dosage correspondingly pushed through the bottom or top of the package.

A unit dosage package is made of any suitable material. In some embodiments instructions for opening a unit cell are included on the cover 206 attached to the unit dosage package. Alternatively, instructions are included below the row 208, the row 216 or on any part of the front of the unit dosage package 210. In some embodiments instructions are separate from, but included with the unit dosage package as part of a kit. Instructions may also be printed on the packaging that comes with the unit dosage package. In some embodiments instructions say something along these lines: (1) push-through black half circle with a key, a pen or a thumbnail; (2) turn card over and peel tab to expose foil; (3) push on plastic blister to dispense. In some embodiments the text "PUSH" or some variation thereof is located on the tabs which open the blisters.

Figure 2B:
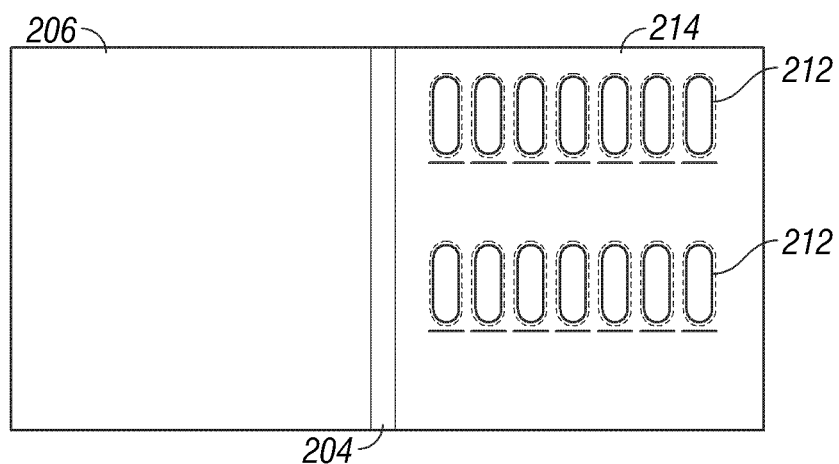
FIG. 2B is a back perspective of the unit dosage package in FIG. 2A.

FIG. 2B illustrates the back of a unit dosage package 214. The back of the unit dosage package 214 is made of any suitable material for a unit dosage package. For example, the backing 212 of each blister 106 may comprise a semi-rigid foil or other material connected to the tab 202 and also to the blister 106. As explained previously, when the tab 202 is pushed through from the front of the unit dosage package to the back of the unit dosage package, the tab 202 is then peeled back, peeling away the backing 212 to expose and/or allow for the pharmaceutical composition to be pushed out of the blister 106. Alternatively, the tab is omitted and the dosage is pushed through the backing without first peeling it back.

In some embodiments multiple drugs are contained within a single blister for release at a specific time. In other embodiments, a single blister contains only a single drug, for example, a single dose of one or more immediate-release formulations. The term "immediate-release" is used herein to specify that the immediate release formulation is not configured to alter the dissolution profile of the formulation. In some embodiments the one or more formulations comprise one or more controlled-release formulations. The term "controlled-release" is used herein in its ordinary sense and thus includes formulations that are combined with ingredients to alter their dissolution profile. A "sustained-release" formulation is a type of controlled-release formulation, wherein ingredients have been added such that the dissolution profile is extended over a longer period of time than that of an immediate release formulation. A "unit dosage" is an amount of drug or drugs taken at a single dosage time. In some embodiments a unit dosage comprises a combination of drugs in a single pharmaceutical formulation or physical form, e.g. a pill or capsule. In some embodiments a unit dosage comprises a combination of drugs in a plurality of separate pharmaceutical formulations or physical forms, e.g. multiple pills or capsules. In some embodiments a single drug is present in a plurality of pharmaceutical formulations or physical forms, e.g. pills or capsules, as a single unit dosage. In some embodiments a unit dosage may be contained within one or more blisters. Thus, in some embodiments, a single blister contains only a single drug, for example, a single dose of sustained-release zonisamide in a single pill or capsule. In other embodiments, a unit dosage of sustained-release zonisamide may be contained within multiple blisters, for example, each containing one or more pills. Thus, in one embodiment two or three of the blisters within a single row or column in a unit dosage package comprise a single unit dosage of a drug.

Figure 3A:
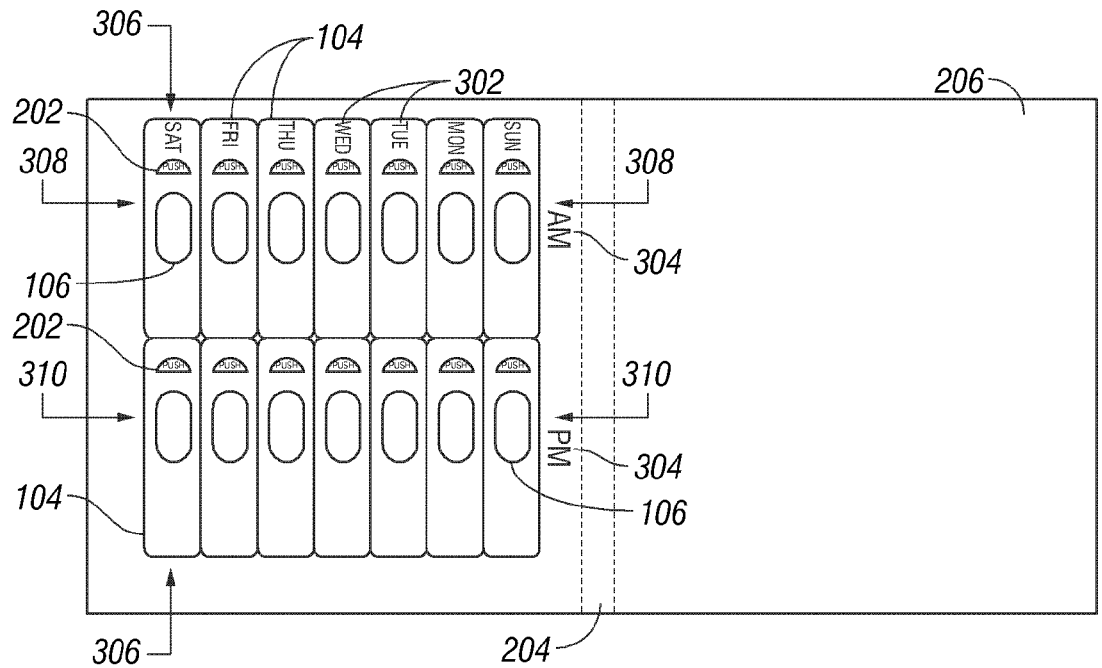
FIG. 3A is a front perspective of an embodiment of a unit dosage package with two rows of unit cells.

FIG. 3A illustrates an embodiment wherein a day label 302 corresponds with a time label 304. The day label 302 additionally corresponds to a unit cell 104 containing a unit dosage. In this embodiment a single blister 106 is contained within a unit cell 104. In the illustrated embodiment a row of blisters 308 corresponds to a specific time label 304 for administration of a medication. As shown in FIG. 3A, a certain day 302 corresponds to a particular administration of one or more unit dosages to a patient. For example, from row 308 and column 306 a first unit dosage corresponds to an AM administration on a Saturday. Later that same day, from row 310 and column 306 (for administration in an evening time), a patient receives a second unit dosage. Thus, a patient uses the unit dosage package to administer the particular drugs for affecting obesity.

In some embodiments, a pharmaceutical composition corresponding to a unit dosage includes a plurality of drugs. In those embodiments, a specific day 302 and time 304 corresponds to a single unit dosage. For example, in one embodiment of a series of unit dosages each dosage comprises a static amount of a first drug and a static amount of a second drug. In another embodiment of a series of unit dosages each dosage comprises a static amount of a first drug and varying dosages of a second drug. In another embodiment of a series of unit dosages each dosage comprises a varying amount of a first drug and a varying amount of a second drug.

In some embodiments, unit dosages on a unit dosage package are sequentially numbered, lettered, or a combination of numbers and letters to indicate an order of administration of each unit dosage. In some embodiments the sequential numbering corresponds to 1, 2, 3, 4, 5, 6, 7, 8, 9, 10, ... n, wherein each number corresponds to a part of, or whole day, week, or month, where "n" is a finite number. For example, in one embodiment, a unit dosage package similar in form to FIG. 3A comprises numerical labels corresponding to the days and times of administration. In this embodiment, no "day labels" or "time labels" are present.

Figure 3B:
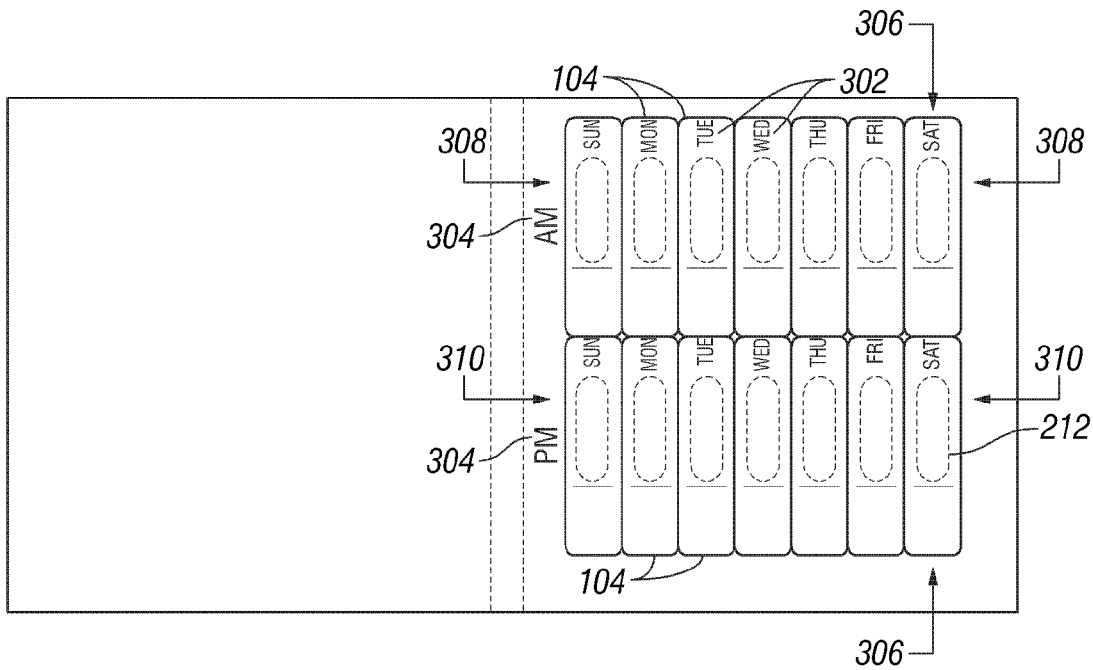
FIG. 3B is a back perspective of the unit dosage package in FIG. 3A.

FIG. 3B illustrates a back of the unit dosage package illustrated in FIG. 3A.

Figure 4A:
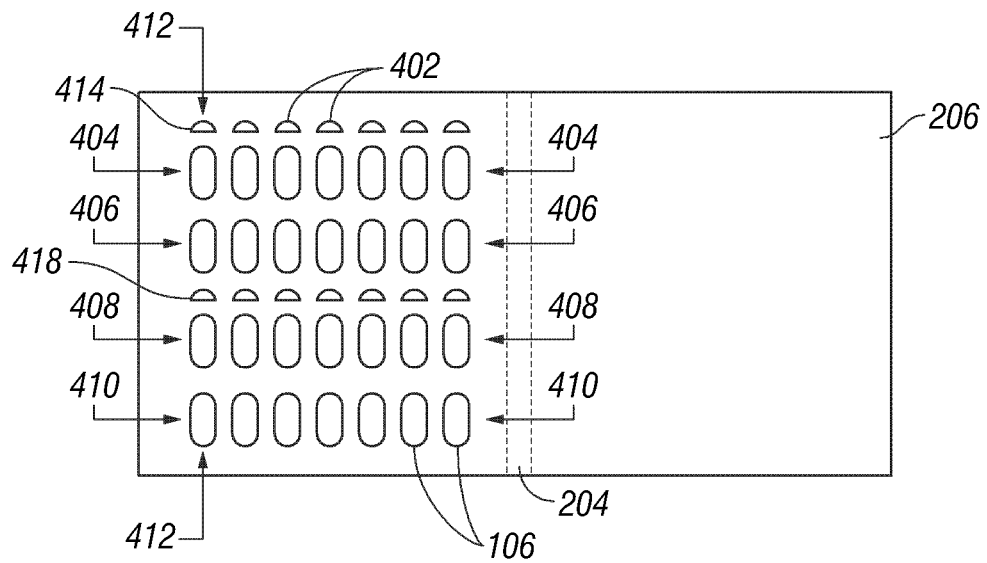
FIG. 4A is a front perspective of an embodiment of a unit dosage package showing four rows of unit cells.

In another embodiment of a unit dosage package FIG. 4A illustrates a series of push-through tabs 402 for opening a plurality of blisters 106. For example, within column 412, blisters from both row 404 and row 406 would be opened by pulling on tab 414 to remove a backing 416 discussed below with reference to FIG. 4B. Similarly, push-through tab 418 would open two blisters 106 within column 412, one from row 408 and one from row 410.

Figure 4B:
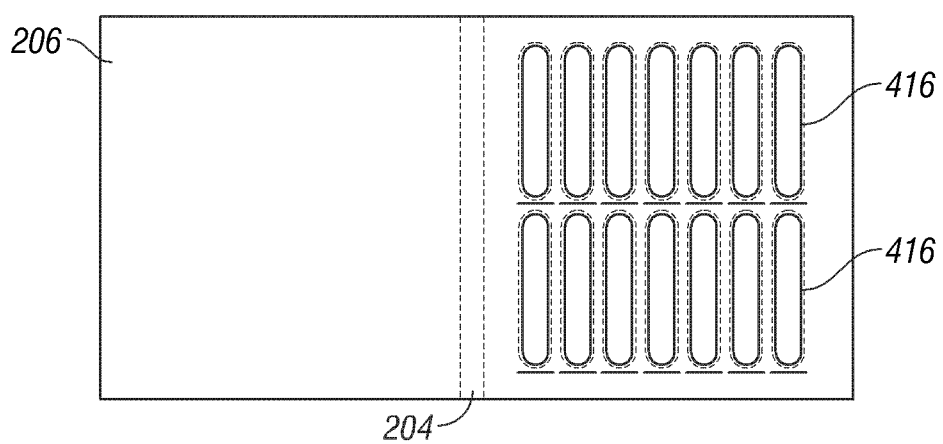
FIG. 4B is a back perspective of the unit dosage package in FIG. 4A.

FIG. 4B illustrates the backing 416 for the unit dosage package in FIG. 4A. The backing 416 allows for a push-through tab 402 to open multiple blisters at a single time.

Figure 5A:
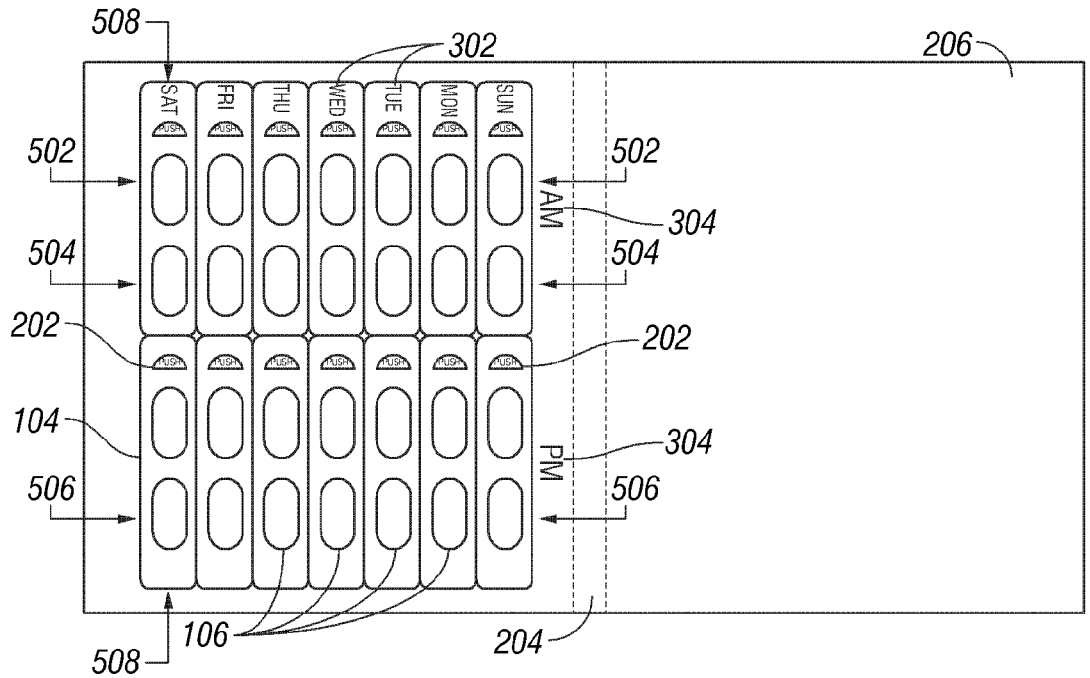
FIG. 5A is a front perspective of an embodiment of a unit dosage package containing four rows of unit cells within two rows of unit cells.

In another embodiment of a unit dosage package illustrated in FIG. 5A, specific day labels 302 on unit cells 104 each correspond to a time label 304 for administration of medication. Here, the time labels 304 shown for administration of medication are AM and PM administrations. In an AM administration, a unit cell 104 comprises a single blister 106 from row 502 and a single blister 106 from row 504. A row of unit cells 104 corresponds to evening administration. Thus, in this embodiment, each unit cell 104 within row 506 contains two blisters 106 for evening administration of a specific pharmaceutical composition.

Further, a unit dosage comprising a combination of drugs within column 508 corresponds to a morning administration and an evening administration on a Saturday. The morning administration comprises one blister 106 from row 502 and one blister 106 from row 504. The combination of medications from rows 502, 504 correspond to a unit dosage of medication for administration on a Saturday morning.

Figure 5B:
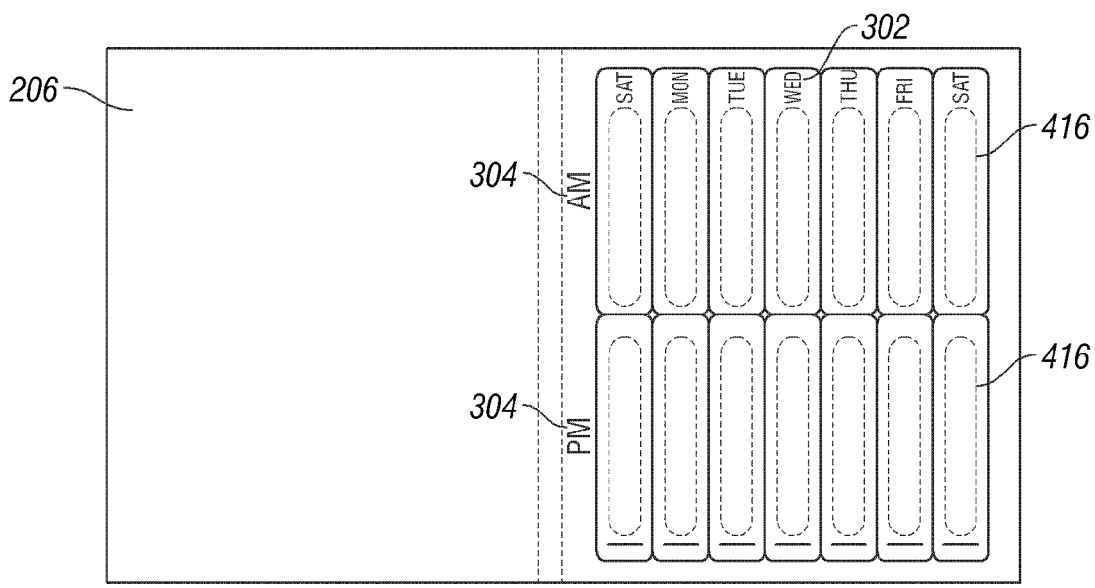
FIG. 5B is a back perspective of the unit dosage package in FIG. 5A.

FIG. 5B illustrates a back of the unit dosage package illustrated in FIG. 5A.

Figure 6A:
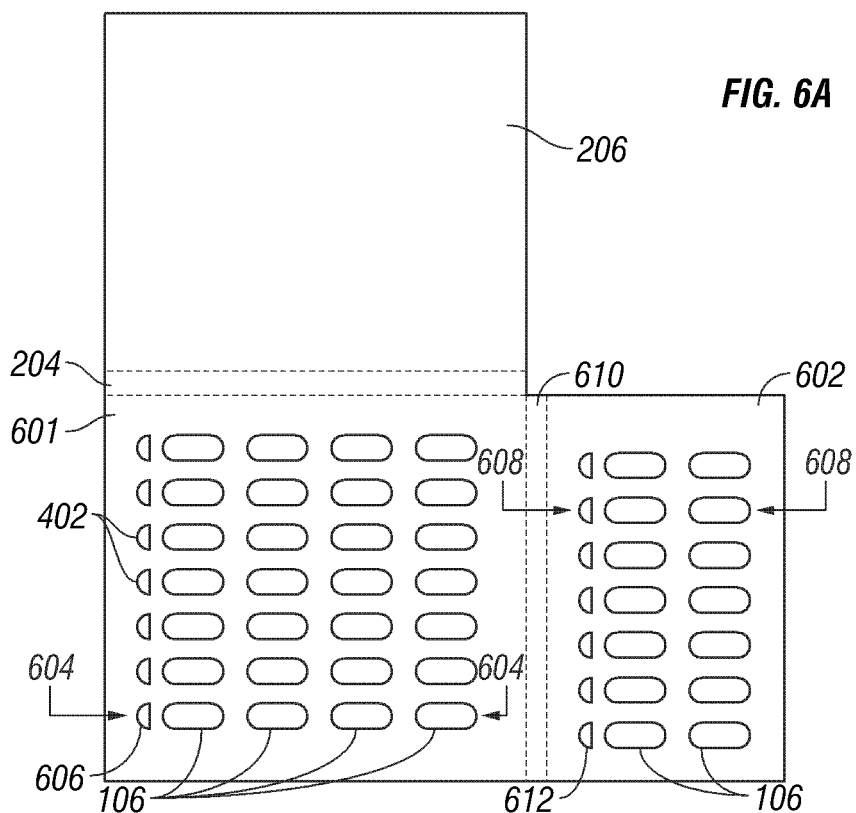
FIG. 6A is a front perspective of an embodiment of a unit dosage package with a second unit dosage package attached.

Another embodiment of a unit dosage package is illustrated in FIG. 6A. The embodiment shows a second unit dosage package 602 attached to a first unit dosage package 601 via a fold 610. The first unit dosage package 601 illustrates a row 604 comprising four blisters 106 wherein a single push-through tab 606 that opens all blisters 106 within the row 604. Similarly, the second unit dosage package 602 contains multiple blisters 106 arranged into rows and columns. A push-through tab 612 for opening a row of blisters 106 is shown on the second unit dosage package 602. The push-through tab 612 would open an entire row, for example, the row 608 on the second unit dosage package 602.

As illustrated in FIG. 6A, a row of blisters 608 on the second unit dosage package 602 contains two blisters 106. A row of blisters 604 on the first unit dosage package 601 contains four blisters. Thus, in some embodiments a single unit dosage package comprises numerous blisters 106. Further, as illustrated in FIG. 6A, each row of blisters 106 is configured to be opened by the push-through tabs 606 or 612.

Figure 6B:
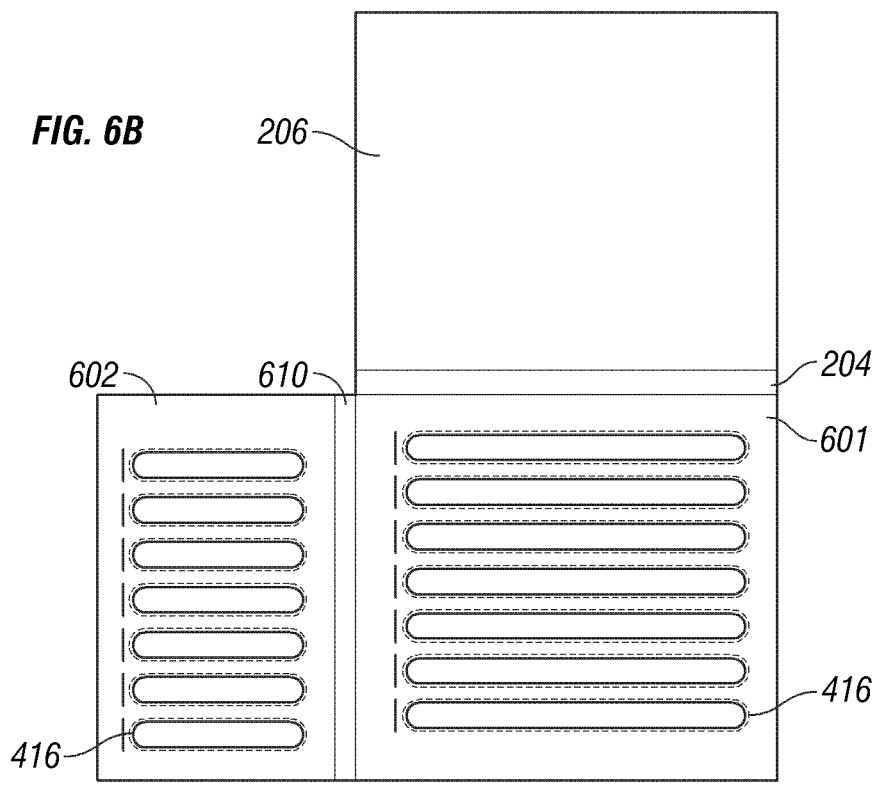
FIG. 6B is a back perspective view of the unit dosage package in FIG. 6A.

FIG. 6B corresponds to a back side of the unit dosage package illustrated in FIG. 6A.

Figure 7A:
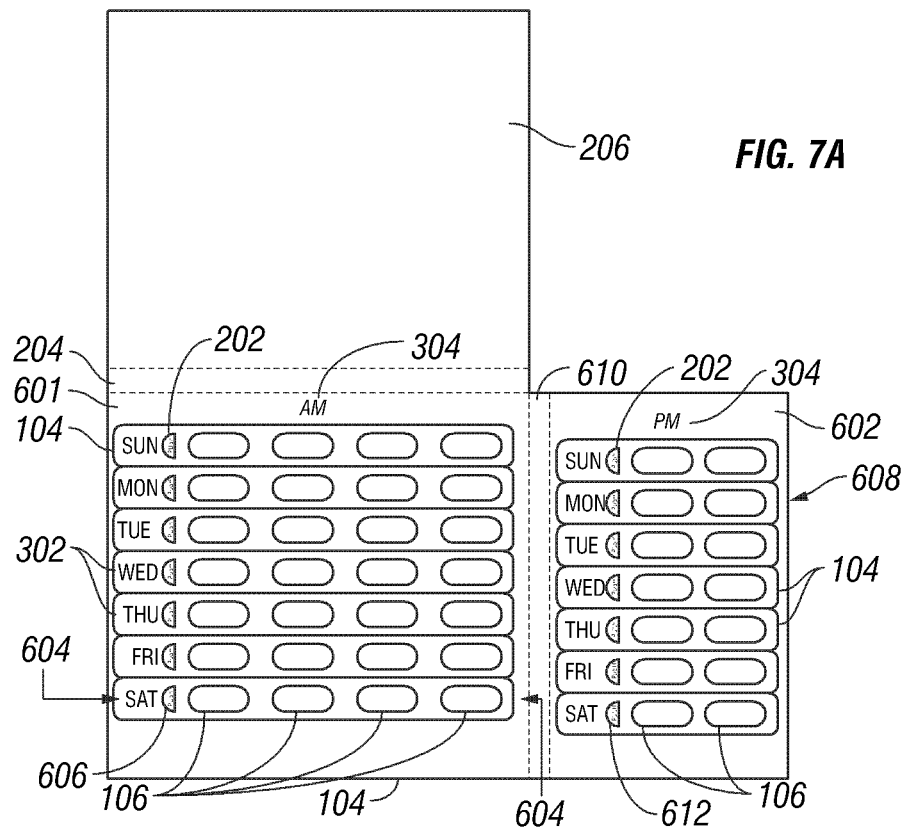
FIG. 7A is a front perspective of an embodiment of a unit dosage package containing six rows of unit cells and two columns of unit cells.

Another embodiment of a unit dosage package is illustrated in FIG. 7A. Similar to the embodiment illustrated in FIG. 6A, a first unit dosage package 601 is attached to a second unit dosage package via a fold 610. The first unit dosage package 601 is also attached to a cover 206 via a fold 204. In some embodiments the cover comprises an instruction sheet. In this embodiment, the first unit dosage package 601 corresponds to AM administration of unit dosages and the second unit dosage package 602 corresponds to PM administration of unit dosages.

Figure 7B:
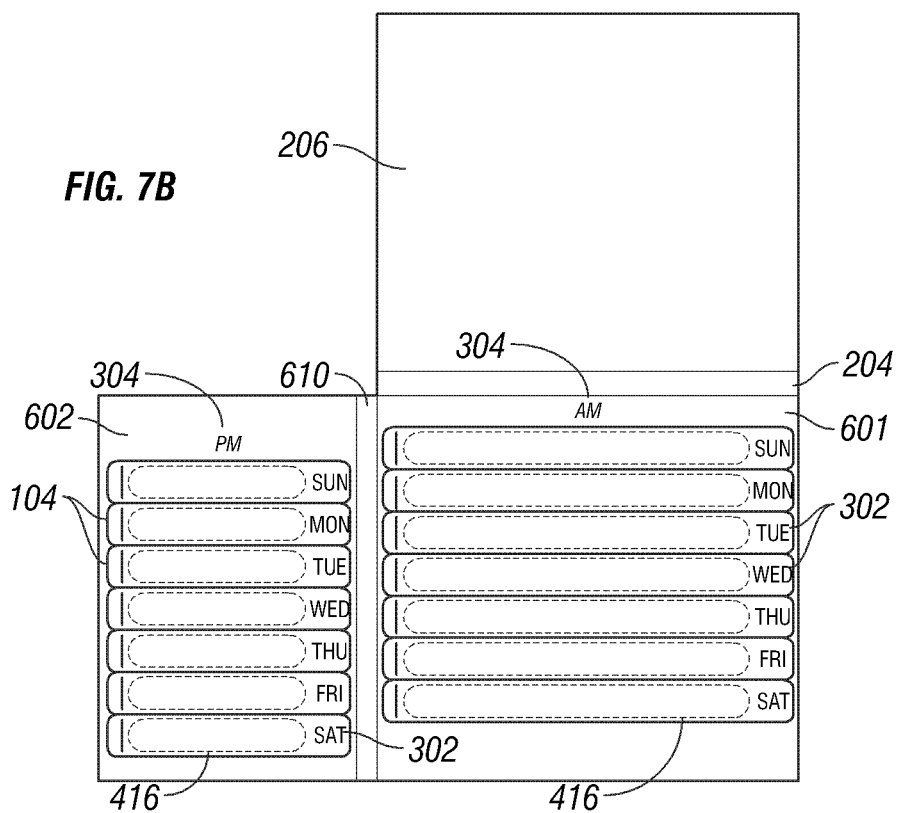
FIG. 7B is a back perspective of the unit dosage package in FIG. 7A.

FIG. 7B illustrates the back side of the unit dosage package in FIG. 7A.

Figure 8A:
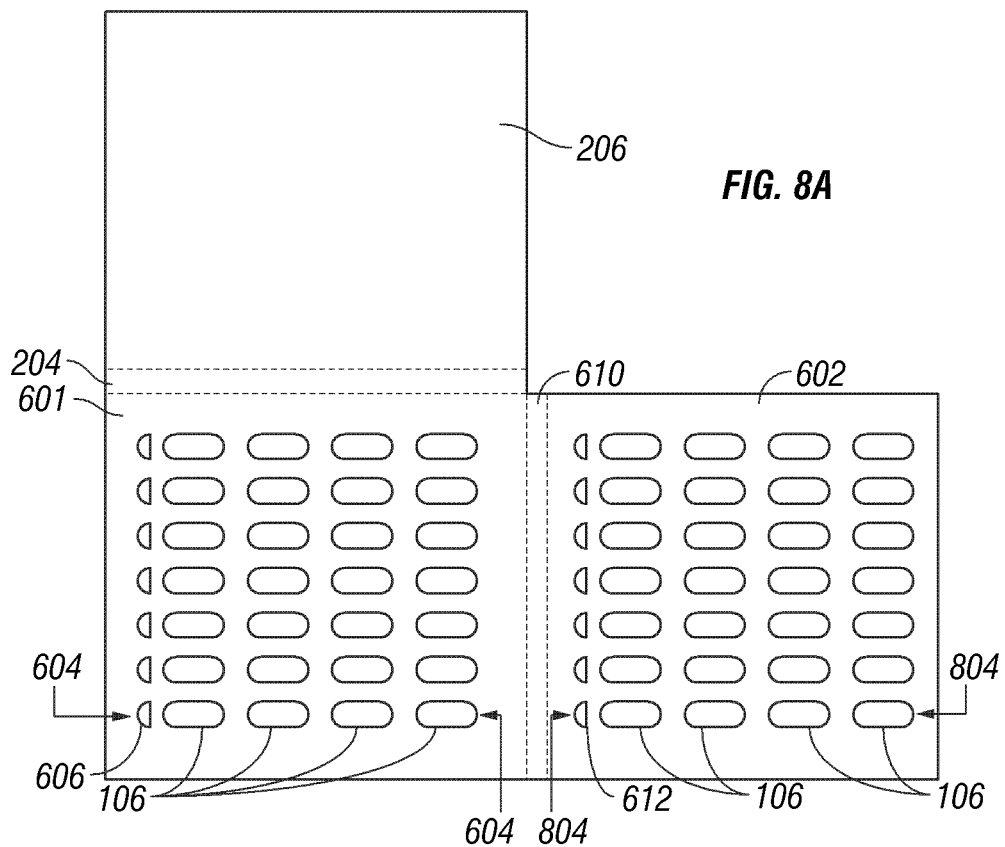
FIG. 8A is a front perspective of an embodiment of a unit dosage package with a second unit dosage package attached.

Similar to the embodiment illustrated in FIG. 7A, FIG. 8A illustrates one embodiment comprising a first unit dosage package 601 attached to a cover 206 via fold 204. The first unit dosage package 601 is also attached to a second unit dosage package 602 via fold 610. Here, the second unit dosage package 602 comprises a row 804 of four blisters 106 wherein a single row of blisters 106 are opened by a single push-through tab 612. FIG. 8A illustrates that a single push-through tab 612 opens all four blisters 106 within a row 804 on the second unit dosage package 602. Similarly, a single push-through tab 606 opens the row 804 of blisters 106 on the first unit dosage package 601.

Figure 8B:
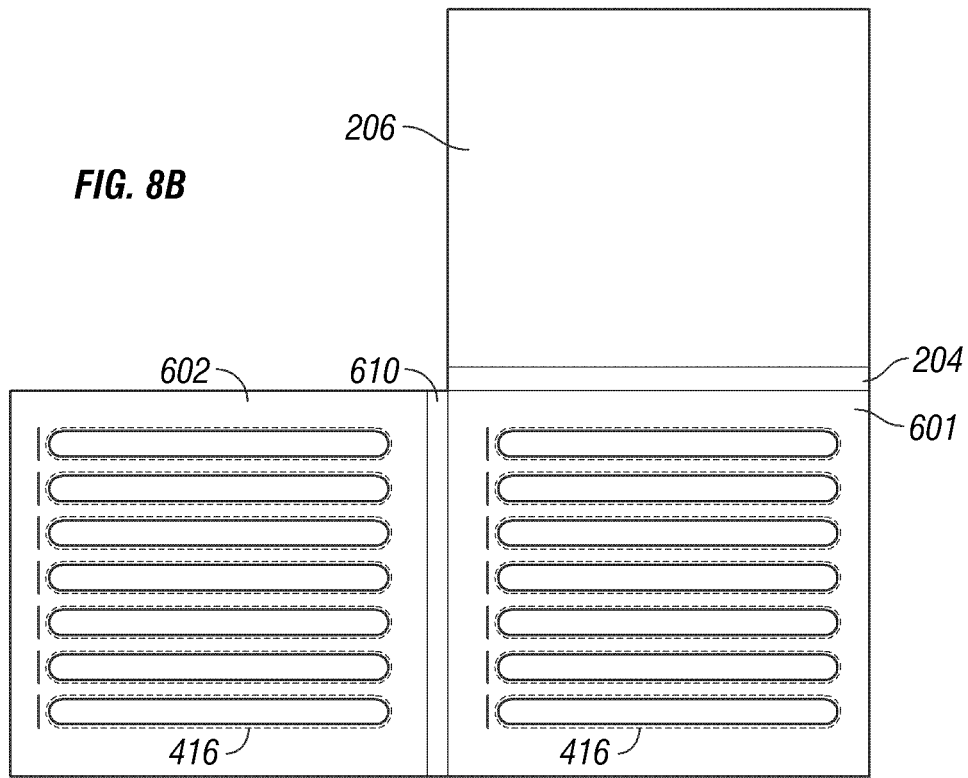
FIG. 8B is a back perspective view of the unit dosage package in FIG. 8A.

FIG. 8B illustrates a back of the unit dosage package in FIG. 8A.

Figure 9A:
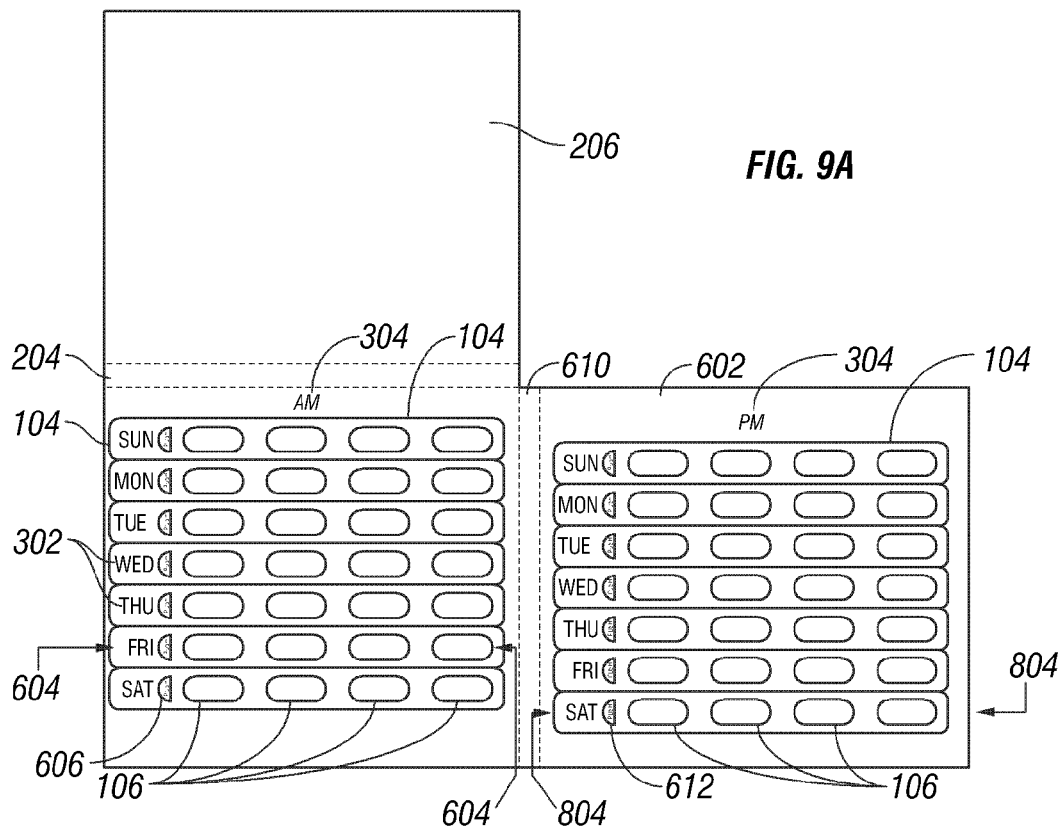
FIG. 9A is a front perspective view of an embodiment of a unit dosage package containing eight rows of blisters and two columns of unit cells.

In another embodiment illustrated in FIG. 9A, the first unit dosage package 601 attached to a cover 206 via a fold 204 corresponds to a time label 304, specifically an AM administration of a drug. The AM dosages for an extra week are arranged in unit cells 104 on the first unit dosage package 601. As in FIG. 8A, opening a single push-through tab 606 exposes drugs contained within a row 604 corresponding to a unit dosage of an AM administration on a Thursday. Similarly, a push-through tab 612 opens all blisters 106 in a unit cell 104 corresponding to the row 804 on Saturday evening. Each day and time listed on the first unit dosage package 601 and the second unit dosage package 602 corresponds to different dosages.

Figure 9B:
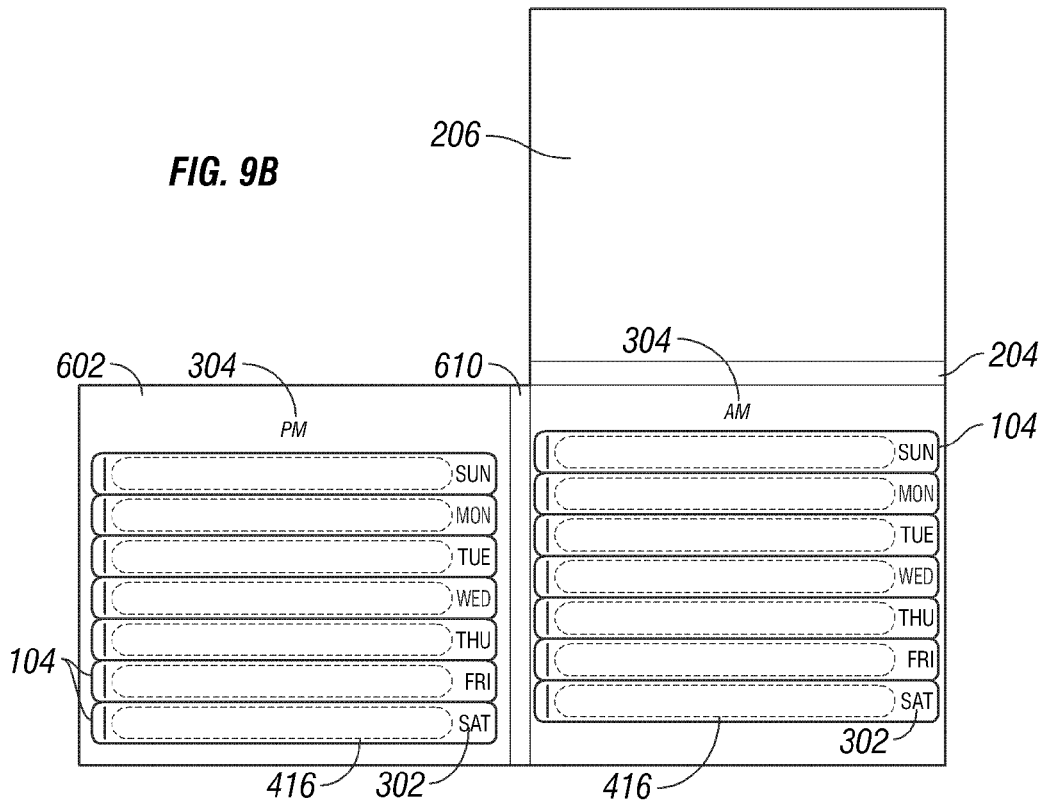
FIG. 9B is a back perspective view of the unit dosage package in FIG. 9A.

FIG. 9B illustrates the back side of the unit dosage package illustrated in FIG. 9A.

In any of the embodiments disclosed herein, the active pharmaceutical ingredients utilized to treat a disease or condition can be selected from any of the compounds below.

Antidepressants and Psychotherapeutics

As mentioned previously, in some embodiments the compositions for the treatment of obesity or for affecting weight loss comprise an antidepressant and at least one of an anticonvulsant and an opioid receptor antagonist. In some embodiments the antidepressant comprises a dopamine reuptake inhibitor or receptor antagonist. Examples of dopamine reuptake inhibitors include phentermine and pharmaceutically acceptable salts or prodrugs thereof. Examples of dopamine receptor antagonists include haloperidol, ocaperidone, risperidone, olanzapine, quetiapine, amisulpride, and pimozide and pharmaceutically acceptable salts or prodrugs thereof. In some embodiments the antidepressant comprises a norepinephrine reuptake inhibitor. Examples of norepinephrine reuptake inhibitors include bupropion, thionisoxetine, atomoxetine and reboxetine and pharmaceutically acceptable salts or prodrugs thereof. Other embodiments include those in which the antidepressant is a dopamine agonist. Dopamine agonists available on the market include cabergoline, amantadine, lisuride, pergolide, ropinirole, pramipexole, and bromocriptine. In some embodiments the antidepressant comprises a serotonin reuptake inhibitor, preferably a selective serotonin reuptake inhibitor (SSRI). Examples of serotonin reuptake inhibitors include fluoxetine and pharmaceutically acceptable salts or prodrugs thereof.

Throughout the disclosure of the present specification the term "pharmaceutically acceptable salt" refers to a formulation of a compound that does not cause significant irritation to an organism to which it is administered and does not abrogate the biological activity and properties of the compound. Pharmaceutical salts can be obtained by reacting a compound of the disclosure with inorganic acids such as hydrochloric acid, hydrobromic acid, sulfuric acid, nitric acid, phosphoric acid, methanesulfonic acid, ethanesulfonic acid, p-toluenesulfonic acid, salicylic acid and the like. Pharmaceutical salts can also be obtained by reacting a compound of the disclosure with a base to form a salt such as ammonium salt, an alkali metal salt such as a sodium or a potassium salt, an alkaline earth metal salt such as a calcium or a magnesium salt, a salt of organic bases such as dicyclohexylamine, N-methyl-D-glucamine, tris(hydroxymethyl)methylamine and salts thereof with amino acids such as arginine, lysine and the like.

The term "prodrug" refers to an agent that is converted into the parent drug in vivo. Prodrugs are often useful because, in some situations, they are easier to administer than the parent drug. They can, for instance, be bioavailable by oral administration whereas the parent is not. The prodrug can also have improved solubility in pharmaceutical compositions over the parent drug or can demonstrate increased palpability or be easier to formulate.

Bupropion, whose chemical name is (±)-1-(3-chlorophenyl)-2-[(1,1-dimethylethyl)amino]-1-propanone, is the active drug in the drugs marketed as ZYBAN® and WELLBUTRIN®, and is usually administered as a hydrochloride salt. Throughout the present disclosure, whenever the term "bupropion" is used, it is understood that the term encompasses bupropion as a free base, or as a physiologically acceptable salt thereof, or as a bupropion metabolite or salt thereof.

The metabolites of bupropion suitable for inclusion in the methods and compositions described herein include the erythro- and threo-amino alcohols of bupropion, the erythroamino diol of bupropion, and morpholinol metabolites of bupropion. In some embodiments, the metabolite of bupropion is (±)-(2R*,3R*)-2-(3-chlorophenyl)-3,5,5-trimethyl-2-morpholinol. In some embodiments the metabolite is (−)-(2R*,3R*)-2-(3-chlorophenyl)-3,5,5-trimethyl-2-morpholinol, while in other embodiments, the metabolite is (+)-(2S,3S)-2-(3-chlorophenyl)-3,5,5-trimethyl-2-morpholinol. Preferably, the metabolite of bupropion is (+)-(2S,3S)-2-(3-chlorophenyl)-3,5,5-trimethyl-2-morpholinol, which is known by its common name of radafaxine. The scope of the present disclosure includes the above-mentioned metabolites of bupropion as a free base or as a physiologically acceptable salt thereof. Controlled-release bupropion formulations of bupropion are known in the art. See, for example, U.S. Pat. No. 6,905,708, which discloses a once-daily dosage configured to deliver bupropion in vivo over a 6 to 12 hour period.

Olanzapine, whose chemical name is 2-methyl-4-(4-methyl-1-piperazinyl)-10H-thieno[2,3-b][1,5]benzodiazepine, is used as a psychotherapeutic agent primarily for the treatment of schizophrenia, acute manic episodes in bipolar disorder acute, maintenance treatment in bipolar disorder and agitation associated with both these disorders. Throughout the present disclosure, whenever the term "olanzapine" is used, it is understood that the term encompasses olanzapine as a free base, or as a physiologically acceptable salt thereof, or as a olanzapine metabolite or salt thereof.

Olanzapine displays linear kinetics. Its elimination half-life ranges from 21 to 54 hours. Steady state plasma concentrations are achieved in about a week. Olanzapine undergoes extensive first pass metabolism and bioavailability is not affected by food.

The psychotherapeutic agent may be selected from the group consisting of mirtazapine, setiptiline, paroxetine, venlafaxine, olanzapine, bupropion, risperidone, lamotrogine, risperidone, a lithium salt, valproic acid, and pharmaceutically acceptable salts or prodrugs thereof. In some embodiments the psychotherapeutic agent is an antidepressant, an antimigrane, an antibipolar, an antimania drug, a mood stabilizer, or an antiepileptic. Examples of antidepressants include paroxetine, mirtazapine, and bupropion. Examples of antibipolar drugs include lithium, valproate, carbamezepine, oxycarbamezepine, lamotrogine, tiagabine, olanzapine, clozapine, risperidone, quetiapine, aripiprazole, ziprasidone, and benzodiazepines. Also included are pharmaceutically acceptable salts or prodrugs of these drugs, extended release or controlled release formulations of the above drugs, as well as combinations of the above drugs.

Fluoxetine is a selective serotonin reuptake inhibitor (SSRI), whose chemical name is N-methyl-3-phenyl-3-[4-(trifluoromethyl)phenoxy]-propan-1-amine, is used primarily for the treatment of depression (including pediatric depression), obsessive-compulsive disorder (in both adult and pediatric populations), bulimia nervosa, panic disorder, premenstrual dysphoric disorder, hypochondriasis and body dysmorphic disorder. Throughout the present disclosure, whenever the term "fluoxetine" is used, it is understood that the term encompasses fluoxetine as a free base, or as a physiologically acceptable salt thereof, or as a fluoxetine metabolite or salt thereof.

Fluoxetine has a bioavailability of approximately 72%, and peak plasma concentrations are reached in 6 to 8 hours. It is highly bound to plasma proteins, mostly albumin. Its elimination half-life ranges from 1 to 3 days—after a single dose—to 4 to 6 days (after long-term use) in healthy adults, and is prolonged in those with liver disease. The half-life of norfluoxetine is longer (16 days after long-term use). Complete excretion of the drug may take several weeks.

The SSRI can be selected from fluoxetine, fluvoxamine, sertraline, paroxetine, citalopram, escitalopram, sibutramine, duloxetine, and venlafaxine, and pharmaceutically acceptable salts or prodrugs thereof. In some embodiments, the SSRI is fluoxetine or a pharmaceutically acceptable salt or prodrug thereof.

Fluoxetine has a physiological half life of about 24 hours, whereas that of naltrexone is about 1.5 hours. However their metabolites may demonstrate half-lives in excess of 24 hours. Thus, in some cases, it may be beneficial to administer one dose of fluoxetine per day in conjunction with two or three or more doses of naltrexone (discussed below) throughout the day. Naltrexone may also be in a time-release formulation where the dose is administered once a day, but naltrexone gradually enters the blood stream throughout the day, or in the course of a 12 hour period.

Symptoms of the obsessive compulsive disorders are inhibited in individuals being administered fluoxetine and naltrexone. Adverse events associated with the obsessive compulsive disorders are reduced in individuals being administered fluoxetine and naltrexone. The effects of administration of both fluoxetine and naltrexone on obsessive compulsive disorder are synergistic compared to effects of those expected by administration of fluoxetine and naltrexone alone.

Newer generation antidepressants include selective serotonin reuptake inhibitors (e.g., fluoxetine, fluvoxamine, sertraline, paroxetine, citalopram, and escitalopram), venlafaxine, duloxetine, nefazodone, mianserin setiptiline, viqualine trazodone, cianopramine, and mirtazapine.

Phentermine is an example of a dopamine reuptake inhibitor with a chemical name 2-methyl-1-phenylpropan-2-amine and 2-methyl-amphetamine. Throughout the present disclosure, whenever the term "phentermine" is used, it is understood that the term encompasses phentermine as a free base, or as a physiologically acceptable salt thereof, or as a phentermine metabolite or salt thereof.

Antidiabetic

In some embodiments an antidiabetic comprises a biguanide, glucosidase inhibitor, insulin, meglitinide, sulfonylurea or a thiazolidinedione. In some embodiments a biguanide comprises metformin hydrochloride. In some embodiments a glucosidase inhibitor includes acarbose and miglitol. Examples of insulin include human insulin, pork insulin, beef insulin, beef-pork insulin, insulin from different sources such as recombinant DNA and animal sources, as well as regular, NPH, and LENTE® types of insulin. Other examples of insulin include mixtures of the various forms of insulin (e.g. NPH and regular human and pork insulin). Other examples of insulin include mixtures of Insulin Lispro Protamine and Insulin Injection (rDNA origin), a 50/50 (or a 70/30) mixture of Human Insulin Isophane Suspension and Human Insulin Injection, a 70/30 mixture of NPH Human Insulin Isophane Suspension and Human Insulin Injection (rDNA), insulin glargine, insulin lispro, insulin aspart, as well as insulin mixed with other ingredients such as zinc crystals or in a phosphate buffer. Insulin may be from *Saccharomyces cerevisiae* or other sources. Examples of meglitinides include nateglinide and repaglinide. Examples of sulfonylureas include glimepiride, glyburide, glibenclamide, gliquidone, gliclazide, chlorpropamide, tolbutamide, tolazamide and glipizide. Examples of thiazolidinediones include rosiglitazone and pioglitazone. Also included are extended release formulations of the above drugs, as well as combinations of the above drugs and pharmaceutically acceptable salts or prodrugs thereof.

As mentioned above, in certain embodiments, the antidiabetic is metformin. Metformin, whose chemical name is 1-(diaminomethylidene)-3,3-dimethyl-guanidine, is often used in the treatment of diabetes mellitus type 2, especially when accompanied obesity and insulin resistance. Metformin has also been proven to reduce the cardiovascular complications of diabetes.

Anticonvulsants

In some embodiments, the anticonvulsant is selected from the group consisting of zonisamide, topiramate, nembutal, lorazepam, clonazepam, clorazepate, tiagabine, gabapentin, fosphenyloin, phenyloin, carbamazepine, balproate, felbamate, lebetiracetam, oxcarbazepine, lamotrigine, methsuximide and ethosuximide.

Zonisamide is a marketed anticonvulsant indicated as adjunctive therapy for adults with partial onset seizures. Without being bound by any particular theory, it is believed that the mechanism of antiepileptic activity appears to be: (1) sodium-channel blocking; and (2) reduction of inward T-type calcium occurrence. In addition, zonisamide binds to the GABA/benzodiazepine receptor complex without producing change in chloride flux. Further, zonisamide facilitates serotonergic and dopaminergic neurotransmission and possesses a weak inhibitory effect on carbonic anhydrase.

Zonisamide has been shown to cause significant weight loss (comparable to marketed weight loss medications) in patients presenting primary obesity. It has been postulated that the affect of zonisamide on the CNS concentration of serotonin, dopamine and carbonic anhydrase is responsible for this effect. There is evidence that zonisamide increases serotonin and dopamine synthesis rates herein. There is further evidence suggesting that zonisamide stimulates dopamine $D_2$ receptors.

Zonisamide can be formulated in an immediate release, a controlled-release and/or sustained-release tablet or gel form. This allows a patient newly prescribed zonisamide to ramp up the dosage level over a period of several days. This increase in dosage form allows the patient to avoid some of the negative side effects that have been exhibited during the initial administration of zonisamide to a patient. Some of these initial side effects include a shock to the body. Although patients who start with a full dose of zonisamide will become acclimated to the dosage over a period of time, the negative side effects accompanying the initial shock to the body can be avoided with a method wherein dosages are increased over a period of several days.

In a pharmaceutical formulation with a drug such as bupropion, a method of administering sustained-release zonisamide by increasing dosages over a period of time can reduce shock to the body while still having a maximum effect for prevention of weight gain and/or treatment of obesity.

In some embodiments, the antidepressant and the anticonvulsant are administered more or less simultaneously. In other embodiments, the antidepressant is administered prior to the anticonvulsant. In yet other embodiments, the antidepressant is administered subsequent to the anticonvulsant.

In certain embodiments, the antidepressant and the anticonvulsant are administered individually. In the other embodiments, the first compound and the anticonvulsant are covalently linked to each other such that they form a single chemical entity. The single chemical entity is then digested and is metabolized into two separate physiologically active chemical entities, one of which is the antidepressant and the other one is the anticonvulsant.

Pharmaceutical preparations of the types found in the unit dosage packages of the present disclosure include forms suitable for packaging within a blister including gel capsules and tablets.

Although the exact dosages will be determined on a drug-by-drug basis, in most cases some generalizations regarding the dosage can be made. Some descriptions of appropriate unit dosages of bupropion, zonisamide, and combinations thereof are disclosed in U.S. Provisional Patent Application Nos. 60/740,034, filed on Nov. 28, 2005; 60/832,110, filed on Jul. 19, 2006; 60/835,564, filed on Aug. 4, 2006; and U.S. patent application Ser. No. 11/194,201 entitled COMBINATION OF BUPROPION AND A SECOND COMPOUND FOR AFFECTING WEIGHT LOSS, filed on Aug. 1, 2005;

which are hereby incorporated by reference in their entireties, and U.S. Patent Publication Nos. 2005/0215552; and 2006/0079501 mentioned previously.

In some embodiments the anticonvulsant is a γ-amino butyric acid (GABA) inhibitor, a GABA receptor antagonist or a GABA channel modulator. By "GABA inhibitor" it is meant a compound that reduces the production of GABA in the cells, reduces the release of GABA from the cells, or reduces the activity of GABA on its receptors, either by preventing the binding of GABA to GABA receptors or by minimizing the effect of such binding. The GABA inhibitor may be a 5-HT1b agonist or another agent that inhibits the activity of NPY/AgRP/GABA neurons. In addition, the GABA inhibitor may suppress the expression of the AgRP gene, or the GABA inhibitor may suppress the production or release of AgRP. It is, however, understood that a 5-HT1b agonist may inhibit the NPY/AgRP/GABA neuron (and therefore activate pro-opiomelanocortin (POMC) neurons) without acting as an inhibitor of the GABA pathway.

In certain other embodiments the GABA inhibitor increases the expression of the POMC gene. In some of these embodiments, the GABA inhibitor increases the production or release of POMC protein. In certain other of these embodiments, the GABA inhibitor increases the activity on POMC expressing neurons.

In some embodiments, the GABA inhibitor is topiramate. Topiramate, whose chemical name is 2,3:4,5-Bis-O-(1-methylethylidene)-beta-D-fructopyranose sulfamate, is often used to treat epilepsy, Lennox-Gastaut syndrome (a disorder causing seizures and developmental delays), neuropathic pain, bipolar disorder, obesity including reduction of binge eating, alcoholism, Post Traumatic Stress Disorder, infantile spasm, bulimia nervosa, or obsessive-compulsive disorder or to assist smoking cessation or prevent migraines. Generally, initial doses of topiramate are low and increased in slow steps. The usual initial dose is 25 to 50 mg daily in 2 single doses. Recommended increments vary, but are usually between 25 mg and 50 mg every 1 or 2 weeks. Common doses for maintenance treatment are 100 to 200 mg daily.

Opioid Receptor Antagonists

In certain embodiments the opioid antagonist antagonizes a μ-opioid receptor (MOP-R) in a mammal. The mammal may be selected from the group consisting of mice, rats, rabbits, guinea pigs, dogs, cats, sheep, goats, cows, primates, such as monkeys, chimpanzees, and apes, and humans.

In some embodiments the opioid antagonist is selected from the group consisting of alvimopan, norbinaltorphimine, nalmefene, naloxone, naltrexone, methylnaltrexone, and nalorphine, and pharmaceutically acceptable salts or prodrugs thereof.

In other embodiments, the opioid antagonist is a partial opioid agonist. Compounds of this class have some agonist activity at opioid receptors. However, because they are weak agonists, they function as de-facto antagonists. Examples of partial opioid agonists include pentacozine, buprenorphine, nalorphine, propiram, and lofexidine.

Naltrexone (17-(cyclopropylmethly)-4,5α-epoxy-3,14-dihydroxymorphinan-6-one) is an opioid receptor antagonist used primarily in the management of alcohol dependence and opioid dependence. μ-subtype selective opioid antagonists such as naltrexone are also of considerable current interest as agents for the treatment of obesity (Glass, M. J.; Billington, C. J.; Levine, A. S. *Neuropeptides* 1999, 33, 350) and CNS disorders (Reneric, J. P.; Bouvard, M. P. *CNS Drugs* 1998, 10, 365).

Naltrexone is marketed as its hydrochloride salt, naltrexone hydrochloride, under the trade name REVIA™. REVIA™ is an immediate release formulation of naltrexone, with 50 mg strength. The maximum serum concentration of immediate release naltrexone is reached very rapidly, typically a $T_{max}$ of approximately 1 hour. Immediate release naltrexone can induce side effects such as nausea, which is attributable to the maximum blood plasma concentration levels ($C_{max}$).

Formulations of sustained-release naltrexone have been disclosed in U.S. Provisional Patent Application Ser. Nos. 60/811,251, filed Jun. 5, 2006; and 60/841,114, filed Aug. 29, 2006; which are hereby incorporated by reference in their entireties. In some embodiments, oral dosage forms of naltrexone are effective to provide an AUC between about 75% to about 125% of 50 mg immediate release naltrexone tablets. In some embodiments oral dosage forms of naltrexone provide an amount of a retardant excipient that is effective to provide a $C_{max}$ that is less than or equal to about 80% of the $C_{max}$ of 50 mg immediate release naltrexone tablets.

Those skilled in the art informed by the guidance provided herein can formulate oral dosage forms described herein. For example, one skilled in the art could formulate an oral dosage form that comprises an amount of naltrexone that is effective to provide an AUC between about 75% to about 125% of 50 mg immediate release naltrexone tablets, and an amount of an appropriate retardant excipient effective to provide a $C_{max}$ that is less than or equal to about 80% of the $C_{max}$ of 50 mg immediate release naltrexone tablets. Further, given the guidance provided herein, the skilled artisan could formulate an oral dosage form having a pharmacodynamic profile characterized by coverage of greater than or equal to about 80% of the opioid receptors in the hypothalamus.

Sustained-Release Zonisamide and Sustained-Release Bupropion

A pharmaceutical formulation comprising sustained-release zonisamide and bupropion can be made in various ways, e.g., by intermixing granules or beads of sustained-release zonisamide with bupropion or sustained-release bupropion, then forming tablets from the mixture in the usual fashion.

A pharmaceutical formulation of zonisamide in combination with bupropion can be used to treat various conditions. For example, an embodiment provides a method for affecting weight loss, increasing energy expenditure, increasing satiety in an individual, and/or suppressing the appetite of an individual, comprising identifying an individual in need thereof and administering effective amounts of sustained-release zonisamide and bupropion. In some embodiments the sustained-release zonisamide and bupropion are administered more or less simultaneously. In other embodiments the sustained-release zonisamide is administered prior to the bupropion. In yet other embodiments, the sustained-release zonisamide is administered subsequent to the bupropion. In other embodiments, one of the compounds is administered while the other compound is being administered.

Sustained-Release Zonisamide and Sustained-Release Naltrexone

In some embodiments naltrexone comprises formulations of either immediate release naltrexone or sustained-release naltrexone. A pharmaceutical formulation comprising sustained-release zonisamide and naltrexone can be made in various ways, e.g., by intermixing granules or beads of sustained-release zonisamide with naltrexone or sustained-release naltrexone, then forming tablets from the mixture in the usual fashion.

Sustained-release zonisamide pharmaceutical formulation can be used in combination with naltrexone to treat various conditions. For example, an embodiment provides a method for affecting weight loss, increasing energy expenditure, increasing satiety in an individual, and/or suppressing the appetite of an individual, comprising identifying an individual in need thereof and administering effective amounts of sustained-release zonisamide and naltrexone. In some embodiments the sustained-release zonisamide and naltrexone are administered more or less simultaneously. In other embodiments the sustained-release zonisamide is administered prior to the naltrexone. In yet other embodiments, the sustained-release zonisamide is administered subsequent to the naltrexone. In other embodiments, one of the compounds is administered while the other compound is being administered.

Sustained-Release Bupropion and Sustained-Release Naltrexone

In some embodiments naltrexone comprises formulations of either immediate release naltrexone or sustained-release naltrexone. In some embodiments bupropion comprises formulations of either immediate release or sustained-release bupropion. A pharmaceutical formulation comprising both bupropion and naltrexone is used in various disclosed embodiments.

Sustained-release bupropion can be used in a pharmaceutical formulation with naltrexone to treat various conditions. For example, an embodiment provides a method for affecting weight loss, increasing energy expenditure, increasing satiety in an individual, and/or suppressing the appetite of an individual. The method comprises identifying an individual in need thereof and administering effective amounts of sustained-release bupropion and naltrexone in a pharmaceutical formulation. In some embodiments the bupropion and naltrexone are administered more or less simultaneously. In other embodiments the bupropion is administered prior to the naltrexone. In yet other embodiments, the bupropion is administered subsequent to the naltrexone. In other embodiments, one of the compounds is administered while the other compound is being administered.

Embodiments

In one embodiment a method of treating a disease or condition comprises identifying a patient suffering from or at risk of said condition. In some embodiments the disease or condition is selected from the group consisting of affecting weight loss, suppressing appetite and treating an obesity-related condition. In one embodiment the method comprises administering to a patient in need thereof a first dosage comprising a first drug and a second drug and administering a second dosage comprising the first drug and the second drug, wherein the second dosage comprises a different amount of the second drug than the first dosage.

In some embodiments the second dosage comprises a greater amount of the second drug than the amount of the second drug in the first dosage. In other embodiments the second dosage comprises a smaller amount of the second drug than the first dosage. In some embodiments the second dosage comprises a different amount of the first drug than the first dosage. In some embodiments the first drug comprises a greater amount in the second dosage than in the first dosage. In other embodiments the first drug comprises a smaller amount in the second dosage than in the first dosage. In some embodiments the first drug comprises a greater amount in the second dosage than in the first dosage and the second drug comprises a greater amount in the second dosage than in the first dosage. In some embodiments the first drug comprises a greater amount in the second dosage than in the first dosage and the second drug comprises a smaller amount in the second dosage than in the first dosage. In some embodiments the first drug comprises a smaller amount in the second dosage than in the first dosage and the second drug comprises a smaller amount in the second dosage than in the first dosage. In any of the embodiments, the change in amount of the first and/or second drug can be continued in the third, fourth, fifth, sixth, seventh or more dosages, until the desired amount is reached, at which point the amount is maintained in subsequent doses. The number of doses which have increasing or decreasing amounts of one drug can be different or the same as the number of doses which have increasing or decreasing amounts of the other drug. One of skill in the art will recognize that the embodiments described herein are not limited to two drug combinations, but can include 3, 4, 5, 6, or more drugs, each independently increasing, decreasing or maintaining the amount of drug in dose.

In some embodiments the obesity-related condition is at least one selected from obesity, hypertension, diabetes, dyslipidaemia, hyperglycemia, weight gain associated with smoking cessation, and weight gain associated with use of a psychotherapeutic drug. In some embodiments the second dosage comprises a greater amount of the second drug than the first dosage. In some embodiments the first drug comprises an antidepressant. In some embodiments the antidepressant comprises bupropion. In some embodiments the bupropion comprises a controlled-release bupropion. In some embodiments the controlled-release bupropion comprises a sustained-release bupropion. In some embodiments the second drug comprises an anticonvulsant. In some embodiments the anticonvulsant comprises zonisamide. In some embodiments the zonisamide comprises a controlled-release zonisamide. In some embodiments the controlled-release zonisamide comprises a sustained-release zonisamide. In some embodiments the second drug comprises an opioid antagonist. In some embodiments the opioid antagonist comprises naltrexone. In some embodiments the naltrexone comprises a controlled-release naltrexone. In some embodiments the controlled-release naltrexone comprises a sustained-release naltrexone.

In some embodiments the first drug comprises an antidepressant and the second drug comprises an anticonvulsant. In some embodiments the antidepressant comprises bupropion and the anticonvulsant comprises zonisamide. In some embodiments the first drug comprises an antidepressant and the second drug comprises an opioid antagonist. In some embodiments the antidepressant comprises bupropion and the opioid antagonist comprises naltrexone.

In some embodiments the method further comprises identifying the patient as being at risk of suffering an adverse side effect from administration of an anticonvulsant. In some embodiments the method further comprises identifying the patient as being at risk of suffering an adverse side effect from administration of an opioid antagonist.

In some embodiments the method further comprises opening a unit dosage package, the unit dosage package comprising the first dosage and the second dosage. In some embodiments the unit dosage package comprises a blister pack. In some embodiments the method further comprises administering a third dosage comprising the first drug and the second drug, wherein the third dosage comprises a greater amount of the second drug than the second dosage. In some embodiments the method further comprises removing the first dosage and the second dosage from the unit dosage package. In some embodiments administering the first dosage comprises administering a tablet that comprises the first drug and the second drug. In some embodiments the tablet comprises a plurality of layers. In some embodiments the tablet is a trilayer tablet. In some embodiments a single blister comprises multiple drugs, wherein each drug is physically separated in physically separate forms, e.g, two or more tablets, capsules, pills, etc.

In some embodiments subsequent administrations of subsequent combinations of the first drug and the second drug are administered. In some embodiments each subsequent combination the dosage of the second drug is increased, e.g., increasing the dosage of the second drug in each subsequent combination of the first drug and the second drug until a full dosage of the second drug is reached. In this manner, the individual can become accustomed to a full dosage combination of the first drug and the second drug through the above method and avoid many of the adverse side effects that could occur if the full dosage had been initially administered. Further, avoiding the adverse side effects reduces premature abandonment of the obesity medication and increases the probability of effecting weight loss in the individual.

In an embodiment a unit dosage package for a pharmaceutical formulation comprises a first unit dosage comprising a first drug and a second drug; a second unit dosage comprising the first drug and the second drug, wherein the second dosage comprises a different amount of the second drug than the first dosage; and a unit dosage package configured to hold the first unit dosage and the second unit dosage.

In some embodiments the second dosage comprises a greater amount of the second drug than the first dosage. In some embodiments the first drug comprises an antidepressant. In some embodiments the antidepressant comprises bupropion. In some embodiments the bupropion comprises a sustained-release bupropion. In some embodiments the second drug comprises an anticonvulsant. In some embodiments the anticonvulsant comprises zonisamide. In some embodiments the zonisamide comprises a sustained-release zonisamide. In some embodiments the second drug comprises an opioid antagonist. In some embodiments the opioid antagonist comprises naltrexone. In some embodiments the naltrexone comprises a sustained-release naltrexone.

In some embodiments the first drug comprises an antidepressant and the second drug comprises an anticonvulsant. In some embodiments the antidepressant comprises bupropion and the anticonvulsant comprises zonisamide. In some embodiments the first drug comprises an antidepressant and the second drug comprises an opioid antagonist. In some embodiments the antidepressant comprises bupropion and the opioid antagonist comprises naltrexone.

In some embodiments the unit dosage package comprises at least one blister and the at least one blister holds both the first drug and the second drug. In some embodiments the unit dosage package comprises a blister pack. In some embodiments at least one of the first unit dosage and the second unit dosage is a multi-layer tablet that comprises the first drug and the second drug. In some embodiments the multi-layer tablet is a trilayer tablet.

Thus, in some preferred embodiments, the multi-layer tablet is useful for the treatment of obesity and/or for affecting weight loss. Some preferred embodiments comprise at least one of an antidepressant and an anticonvulsant. Other preferred embodiments comprise at least one of an antidepressant and an opioid receptor antagonist. Other preferred embodiments comprise at least one of an anticonvulsant and an opioid receptor antagonist. Other preferred embodiments comprise at least one of an anticonvulsant and an antidiabetic.

In some embodiments, one or more of the drugs comprises naltrexone and one or more of the drugs comprises fluoxetine. In another embodiment, one or more of the drugs comprises olanzapine and one or more of the drugs comprises zonisamide. In another embodiment, one or more of the drugs comprises metformin and one or more of the drugs comprises zonisamide. In another embodiment, one or more of drugs comprises phentermine and one or more of the drugs comprise topiramate.

In some embodiments the presence of one drug in a pharmaceutical formulation enhances the desired physiological effects and/or reduces undesired physiological effects of one or more other drugs in the pharmaceutical formulation. In some embodiments the presence of one or more drugs in a pharmaceutical formulation enhances the desired physiological effects of the drugs over the additive physiological effects of the one or more drugs in comparable pharmaceutical formulations when administered alone.

Pharmaceutical formulations of any drug mentioned herein can be configured in various ways and in a variety of dosage forms to modify a dissolution rate of the drug. For example, one type of controlled-release pharmaceutical formulation is a sustained-release pharmaceutical formulation. Sustained-release pharmaceutical formulations can contain a variety of excipients, such as retardant excipients (also referred to as release modifiers) and/or fillers that are selected and incorporated into the formulation in such a way as to slow the dissolution rate of the formulation (and thereby slow the dissolution and/or release of the zonisamide) under in vivo conditions as compared to an otherwise comparable immediate-release formulation. Thus, a "comparable" immediate-release formulation is one that is substantially identical to the controlled-release formulation, except that that it is configured to provide immediate-release instead of controlled-release under substantially identical conditions.

The term "immediate-release" is used herein to specify a formulation that is not configured to alter the dissolution profile of the active ingredient (e.g., zonisamide, bupropion, naltrexone, olanzapine, phentermine, topiramate, metformin, fluoxetine). For example, an immediate-release pharmaceutical formulation may be a pharmaceutical formulation that does not contain ingredients that have been included for the purpose of altering the dissolution profile. An immediate-release formulation thus includes drug formulations that take less than 30 minutes for substantially complete dissolution of the drug in a standard dissolution test. A "standard dissolution test," as that term is used herein, is a test conducted according to United States Pharmacopeia 24th edition (2000) (USP 24), pp. 1941-1943, using Apparatus 2 described therein at a spindle rotation speed of 100 rpm and a dissolution medium of water, at 37° C., or other test conditions substantially equivalent thereto. The term "controlled-release" is used herein in its ordinary sense and thus includes pharmaceutical formulations that are combined with ingredients to alter their dissolution profile. A "sustained-release" formulation is a type of controlled-release formulation, wherein ingredients have been added to a pharmaceutical formulation such that the dissolution profile of the active ingredient is extended over a longer period of time than that of an otherwise comparable immediate-release formulation. A controlled-release formulation thus includes drug formulations that take 30 minutes or longer for substantially complete dissolution of the drug in a standard dissolution test, conditions which are representative of the in vivo release profile.

In an embodiment a method of packaging a combination of bupropion and at least one of zonisamide and naltrexone comprises providing a unit dosage package that holds the bupropion and the at least one of the zonisamide and the naltrexone; and packaging administration instructions with the unit dosage package in a unit dosage package.

In some embodiments the bupropion comprises a sustained-release bupropion. In some embodiments the zonisamide comprises a sustained-release zonisamide. In some embodiments the naltrexone comprises a sustained-release naltrexone. In some embodiments packaging administration instructions in the unit dosage package comprises printing instructions onto the unit dosage package. In some embodiments the unit dosage package comprises a blister pack.

In some embodiments, the method is realized by a medical professional e.g., a physician or a hospital employee. The medical professional administers each dosage, a "unit dosage" (as defined herein), of the first drug and the second drug to the individual in need of such treatment. Each succeeding unit dosage combination contains an increased dosage of the second drug until a full dosage of the first drug in combination with the second drug is reached.

In one embodiment of the method the medical professional employs a unit dosage package. The unit dosage package contains a number of "unit dosages", each representing a single administration of a particular pharmaceutical formulation. In some embodiments the pharmaceutical formulation comprises a specific combination of a first drug and a second drug. The pharmaceutical formulation may be a single pill, capsule, tablet, etc. or may be a plurality of pills, capsules, tablets, etc. Each successive pharmaceutical formulation in a unit dosage package ramps up the dosage of the second drug until a full dosage is reached. In this manner, at a first administration a medical professional removes a first pharmaceutical formulation dosage from the unit dosage package and administers the first dosage to an individual. At a second administration the medical professional removes a second pharmaceutical formulation dosage from the unit dosage package and administers the second dosage to the individual. At subsequent administrations the medical professional removes and administers successive pharmaceutical formulation dosages until a full dosage of the second drug in combination with the first drug is reached. The medical professional is thus able to perform one embodiment of the method.

Another embodiment provides a system for performing the method by an individual without the constant supervision of a medical professional. An individual is provided with a unit dosage package comprising a unit dosage package. The unit dosage package comprises a number of dosages, each dosage representing a pharmaceutical formulation. The pharmaceutical formulations comprise varying combinations of a first drug and a second drug. In preferred embodiments the dosages are arranged within the unit dosage package so that each successive pharmaceutical formulation contains increased amounts of the second drug in combination with constant amounts of the first drug e.g., until a full dosage of the second drug is reached. On a first day, the individual removes the first pharmaceutical formulation from the unit dosage package and ingests it. On a second day, based on the structure of the unit dosage package, the individual removes a second pharmaceutical formulation and ingests it. In some embodiments each successive dosage is labeled sequentially with numbers or letters, or a combination of the two. In some embodiments each successive dosage corresponds to a day or time label. In preferred embodiments the second pharmaceutical formulation and each successive formulation in the unit dosage package comprise an increased amount of the second drug until a full dosage is reached. Some embodiments of a unit dosage package also comprise instructions to the individual for administration of each successive pharmaceutical formulation. The individual becomes accustomed to increased pharmaceutical formulations dosages. Thus, the individual can use the unit dosage package to decrease or avoid many of the initial adverse side effects associated with administering a full dosage combination of the first drug and the second drug to affect weight loss.

It may be convenient for a consumer to have a unit dosage package that designates a particular length of time for administration of one or more drugs. For example, a particular unit dosage package may comprise a month of unit dosages. Another unit dosage package may comprise a week of unit dosages. Another unit dosage package may comprise two or more days of unit dosages. A unit dosage package may also comprise detachable strips representing smaller lengths of time. For example, a unit dosage package representing two or more weeks may comprise two or more portions that may be detached to form individual unit dosage packages.

Certain embodiments of unit dosage packages are known in the art. See, for example, U.S. Pat. No. 3,942,641, wherein it is indicated that unit dosage packages include those that accommodate pharmaceutical formulations representing daily unit dosage forms in a contiguous, sequential arrangement which, if properly used according to instructions packaged therewith, cause the proper formulation to be administered at the appropriate time. For example, such a unit dosage package can comprise individual blister pods ("blisters") for the storage in each of a single unit dosage form. At the appropriate time the unit dosage form is manually dispensed therefrom through a frangible retaining layer. Storage of other unit dosage forms is not affected by such dispensing. Appropriate notations are placed on the unit dosage package or the unit dosage package, if desired, to guide or instruct the user thereof in the proper use of the pharmaceutical formulations contained therein. For example, day of the week, miscellaneous instructions, etc., are provided, if so desired.

In some embodiments a unit dosage package comprises a number of blisters. Blisters comprise unit dosages. Unit dosages of pharmaceutical formulations comprising at least a first drug and a second drug are thus administered from the unit dosage package. In some embodiments, a single blister contains a unit dosage of both the first drug and the second drug. In other embodiments a single blister contains either a unit dosage of a first drug or a unit dosage of a second drug. (In the latter case a corresponding blister can contain a corresponding dosage of the other.)

In some embodiments a unit dosage package is a blister pack, a pill box or a medication dispenser. Examples of pill boxes include a wallet card pill carrier, a key ring pill box, a capsule shaped pill box, a hollow necklace dispenser, a weekly organizer, an organizer cube, an airtight box and a hollow pocket watch. Examples of medication dispensers include certain types of unit dosage packages that hold certain medications in a specific order for accurate administration. In some embodiments a unit dosage package has compartments holding specific unit dosages and/or combinations of pharmaceutical formulations including prescribed medications suitable for administration to a patient. Some unit dosage packages include instructions for medication administration.

In some embodiments, the dosages are provided at least once, twice or three times a day for a set period, which can be at least, at least about, less than, less than about, equal to or between any range within 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive days or at least, at least about, less than, less than about, equal to or between any range within of 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive weeks or at least, at least about, less than, less than about, equal to or between any range within 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 consecutive months. The amount of drug in any pharmaceutical formulation described herein includes amounts of at least, at least about, less than, less than about, equal to or between any range within 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 15, 20, 25, 30, 35, 40, 45, 50, 55, 60, 65, 70, 75, 80, 85, 90, 95, 100, 125, 150, 175, 200, 250, 300, 350, 400, 450, 500, 550, 600, 650, 700, 750, 800, 850, 900, 950, 1000, 1500, 2000, 3000, 4000 or 5000 mg.

In one embodiment a unit dosage package for a pharmaceutical formulation, comprises a first unit dosage comprising a first drug and a second drug, a second unit dosage comprising the first drug and the second drug, wherein the second unit dosage comprises a different amount of the second drug than the first unit dosage and a unit dosage package configured to hold the first unit dosage and the second unit dosage.

In some embodiments the second unit dosage comprises a greater amount of the second drug than the first unit dosage. In some embodiments the first drug or the second drug comprises an antidepressant. In some embodiments the antidepressant comprises bupropion. In some embodiments the bupropion comprises a sustained-release bupropion. In some embodiments the first drug or the second drug comprises an anticonvulsant. In some embodiments the anticonvulsant comprises zonisamide. In some embodiments the zonisamide comprises a sustained-release zonisamide. In some embodiments the first drug or the second drug comprises an opioid antagonist. In some embodiments the opioid antagonist comprises naltrexone.

In some embodiments the first drug comprises bupropion and the second drug comprises zonisamide. In some embodiments the first drug comprises bupropion and the second drug comprises naltrexone. In some embodiments the first drug comprises fluoxetine and the second drug comprises naltrexone. In some embodiments the first drug comprises olanzapine and the second drug comprises zonisamide. In some embodiments the first drug comprises antidiabetic and the second drug comprises zonisamide. In some embodiments the antidiabetic comprises metformin. In some embodiments the first drug comprises topiramate and the second drug comprises phentermine. In some embodiments the unit dosage package comprises a blister and the blister holds both the first drug and the second drug.

In some embodiments the first drug and the second drug are selected from the group consisting of zonisamide, bupropion, naltrexone, phentermine, topiramate, metformin, olanzapine, fluoxetine, and any combinations, prodrugs or salts thereof. In some embodiments the first drug and the second drug are part of a single physical form. In some embodiments the single physical form is a multi-layer tablet. In some embodiments the multi-layer tablet is a trilayer tablet. In some embodiments the unit dosage package comprises a first blister and a second blister, wherein the first blister holds the first drug and the second blister holds the second drug. In some embodiments the unit dosage package comprises a blister pack.

In one embodiment a method of providing a pharmaceutical formulation to a patient comprises providing a unit dosage package for a pharmaceutical formulation, wherein the unit dosage package is configured to hold a first unit dosage and a second unit dosage, wherein the first unit dosage comprises a first drug and a second drug, wherein the second unit dosage comprises the first drug and the second drug, and wherein the second unit dosage comprises a different amount of the second drug than the first unit dosage.

In some embodiments the method further comprises identifying a patient with an obesity related condition, wherein the obesity-related condition is selected from the group consisting of obesity, hypertension, diabetes, dyslipidaemia, weight gain associated with smoking cessation and weight gain associated with use of a psychotherapeutic drug. In some embodiments the second dosage comprises a greater amount of the second drug than the first dosage.

In some embodiments the first drug or the second drug comprises an antidepressant. In some embodiments the first drug or the second drug comprises an anticonvulsant. In some embodiments the first drug or the second drug comprises an opioid antagonist. In some embodiments the first drug or the second drug comprises an antidiabetic. In some embodiments the first drug and the second drug are selected from the group consisting of zonisamide, bupropion, naltrexone, phentermine, topiramate, antidiabetic, olanzapine, fluoxetine, and any combinations, prodrugs or salts thereof.

In some embodiments the method further comprises identifying the patient as being at risk of suffering an adverse side effect from administration of an anticonvulsant. In some embodiments the method further comprises identifying the patient as being at risk of suffering an adverse side effect from administration of an opioid antagonist. In some embodiments the method further comprises opening a unit dosage package, the unit dosage package comprising the first dosage and the second dosage. In some embodiments the unit dosage package comprises a blister pack.

In some embodiments the unit dosage package comprises a third unit dosage and, wherein the third dosage comprises a greater amount of the second drug than the second dosage. In some embodiments providing the unit dosage package comprises removing the first dosage and the second dosage from the unit dosage package. In some embodiments providing a unit dosage package comprises administering a tablet that comprises the first drug and the second drug to the patient, wherein the tablet comprises a plurality of layers. In some embodiments the tablet is a trilayer tablet.

It will be appreciated by those skilled in the art that various modifications and changes can be made without departing from the scope of the invention. Such modifications and changes are intended to fall within the scope of the invention, as defined by the appended claims.

What is claimed is:

1. A method of administering a pharmaceutical formulation to an individual, comprising:
   administering a first amount of a pharmaceutical formulation every day for a first week, wherein the first amount of a pharmaceutical formulation comprises about 90 mg of bupropion and an amount of naltrexone selected from the group consisting of about 4 mg and about 8 mg;
   administering a second amount of a pharmaceutical formulation every day for a second week, wherein the second amount of a pharmaceutical formulation comprises bupropion and naltrexone, and wherein the second amount of a pharmaceutical formulation comprises about twice as much bupropion and about twice as much naltrexone as the first amount of a pharmaceutical formulation;
   administering a third amount of a pharmaceutical formulation every day for a third week, wherein the third amount of a pharmaceutical formulation comprises bupropion and naltrexone, and wherein the third amount of a pharmaceutical formulation comprises about three times as much bupropion and about three times as much naltrexone as the first amount of a pharmaceutical formulation; and administering a fourth amount of a pharmaceutical formulation every day for a fourth week, wherein the fourth amount of a pharmaceutical formulation comprises bupropion and naltrexone, and wherein the fourth amount of a pharmaceutical formulation comprises about four times as much bupropion and about four times as much naltrexone as the first amount of a pharmaceutical formulation.

2. The method of claim 1, wherein the first amount of a pharmaceutical formulation comprises about 8 mg naltrexone.

3. The method of claim 1, wherein the first amount of a pharmaceutical formulation comprises about 4 mg naltrexone.

4. The method of claim 1, wherein the first amount of a pharmaceutical formulation is in a single oral dosage form.

5. The method of claim 4, wherein the single oral dosage form is selected from the group consisting of a tablet, a pill and a capsule.

6. The method of claim 4, wherein the second amount of a pharmaceutical formulation comprises two of the single oral dosage forms.

7. The method of claim 6, wherein the third amount of a pharmaceutical formulation comprises three of the single oral dosage forms.

8. The method of claim 7, wherein the fourth amount of a pharmaceutical formulation comprises four of the single oral dosage forms.

9. The method of claim 1, wherein the bupropion is in a sustained release formulation and the naltrexone is in a sustained release formulation.

10. The method of claim 9, wherein the first amount of a pharmaceutical formulation is in a single oral dosage form,
wherein the second amount of a pharmaceutical formulation comprises two of the single oral dosage forms,
wherein the third amount of a pharmaceutical formulation comprises three of the single oral dosage forms, and
wherein the fourth amount of a pharmaceutical formulation comprises four of the single oral dosage forms.

11. The method of claim 10, wherein the single oral dosage form is a multilayer tablet comprising a first pharmaceutical layer comprising the sustained release formulation of bupropion and a second pharmaceutical layer comprising the sustained release formulation of naltrexone, and an intermediate layer between the first and the second pharmaceutical layers, wherein the intermediate layer is configured to dissolve rapidly in vivo.

12. The method of claim 9, wherein the first amount of a pharmaceutical formulation consists of two single oral dosages forms, the sustained release bupropion in a first single oral dosage form and the sustained release naltrexone in a second single oral dosage form,
wherein the second amount of a pharmaceutical formulation consists of two of the first single oral dosage forms and two of the second single oral dosage forms,
wherein the third amount of a pharmaceutical formulation consists of three of the first single oral dosage forms and three of the second single oral dosage forms, and
wherein the fourth amount of a pharmaceutical formulation consists of four of the first single oral dosage forms and four of the second single oral dosage forms.

13. The method of claim 9, wherein the first amount of a pharmaceutical formulation consists of two single oral dosages forms, the sustained release bupropion having a first single oral dosage form and the sustained release naltrexone having a second single oral dosage form,
wherein the second amount of a pharmaceutical formulation consists of two single oral dosages forms, the sustained release bupropion having a third single oral dosage form, and the sustained release naltrexone having a fourth single oral dosage form, and
wherein the third amount of a pharmaceutical formulation consists of two single oral dosages forms, the sustained release bupropion having the first single oral dosage form and the third single oral dosage form, and the sustained release naltrexone having the second single oral dosage form and the fourth single oral dosage form,
wherein the fourth amount of a pharmaceutical formulation consists of two of the third single oral dosage forms and two of the fourth single oral dosage forms.

14. The method of claim 1, further comprising identifying said individual as obese, and said administering of said pharmaceutical formulation is for treatment of obesity.

15. The method of claim 10, further comprising identifying said individual as obese, and said administering of said pharmaceutical formulation is for treatment of obesity.

16. The method of claim 11, further comprising identifying said individual as obese, and said administering of said pharmaceutical formulation is for treatment of obesity.

17. A method of administering a pharmaceutical formulation to an obese individual, comprising:
identifying an individual as obese;
providing to the individual a first amount of a pharmaceutical formulation for daily administration during a first week, wherein the first amount of a pharmaceutical formulation comprises about 90 mg of bupropion and an amount of naltrexone selected from the group consisting of about 4 mg and about 8 mg, wherein the bupropion is in a sustained release formulation and the naltrexone is in a sustained release formulation, and wherein the first amount of a pharmaceutical formulation is in a single oral dosage form;
providing to the individual a second amount of a pharmaceutical formulation for daily administration during a second week, and wherein the second amount of a pharmaceutical formulation comprises about twice as much bupropion and about twice as much naltrexone as the first amount of a pharmaceutical formulation;
providing to the individual a third amount of a pharmaceutical formulation for daily administration during a third week, wherein the third amount of a pharmaceutical formulation comprises about three times as much bupropion and about three times as much naltrexone as the first amount of a pharmaceutical formulation; and
providing to the individual a fourth amount of a pharmaceutical formulation for daily administration during a fourth week, wherein the fourth amount of a pharmaceutical formulation comprises about four times as much bupropion and about four times as much naltrexone as the first amount of a pharmaceutical formulation, and
wherein the providing of the first amount of a pharmaceutical formulation, the second amount of a pharmaceutical formulation, the third amount of a pharmaceutical formulation and the fourth amount of a pharmaceutical formulation are for treatment of obesity.

* * * * *